(12) United States Patent
Doremaele et al.

(10) Patent No.: US 9,994,647 B2
(45) Date of Patent: Jun. 12, 2018

(54) METAL COMPLEX WITH A CYCLIC AMIDINE LIGAND

(71) Applicant: ARLANXEO NETHERLANDS B.V., Geleen (NL)

(72) Inventors: Van Gerardus Henricus Josephus Doremaele, Sittard (NL); Alexandra Berthoud, Neerharen (BE); Victor Quiroga Norambuena, Lanaken (BE); Leszek Rupnicki, Maastricht (NL); Peter Karbaum, Bonn (DE)

(73) Assignee: ARLANXEO NETHERLANDS B.V., Geleen (NL)

( * ) Notice: Subject to any disclaimer, the term of this patent is extended or adjusted under 35 U.S.C. 154(b) by 0 days. days.

(21) Appl. No.: 15/114,903

(22) PCT Filed: Jan. 27, 2015

(86) PCT No.: PCT/EP2015/051571
§ 371 (c)(1),
(2) Date: Jul. 28, 2016

(87) PCT Pub. No.: WO2015/113957
PCT Pub. Date: Aug. 6, 2015

(65) Prior Publication Data
US 2016/0347873 A1 Dec. 1, 2016

(30) Foreign Application Priority Data
Jan. 29, 2014 (EP) .................................... 14153077

(51) Int. Cl.
| | | |
|---|---|---|
| C08F 4/76 | (2006.01) | |
| C08F 4/64 | (2006.01) | |
| C08F 4/6592 | (2006.01) | |
| C08F 210/16 | (2006.01) | |
| C07F 7/28 | (2006.01) | |
| C08F 210/18 | (2006.01) | |
| C08F 4/659 | (2006.01) | |

(52) U.S. Cl.
CPC .............. *C08F 4/6592* (2013.01); *C07F 7/28* (2013.01); *C08F 210/16* (2013.01); *C08F 210/18* (2013.01); *C08F 4/65912* (2013.01); *C08F 2420/04* (2013.01)

(58) Field of Classification Search
CPC .......... C08F 4/64044; C08F 4/76; C08F 4/64; C08F 210/16
See application file for complete search history.

(56) References Cited

U.S. PATENT DOCUMENTS

| | | | | |
|---|---|---|---|---|
| 5,502,128 A | * | 3/1996 | Flores ................... | B01J 31/1805 502/349 |
| 7,053,157 B2 | * | 5/2006 | Sita .......................... | C08F 10/00 526/113 |
| 7,183,364 B2 | * | 2/2007 | Sita .......................... | C08F 10/00 526/161 |
| 8,546,276 B2 | * | 10/2013 | Gatineau ................. | C23C 16/34 427/250 |

(Continued)

FOREIGN PATENT DOCUMENTS

| | | | | |
|---|---|---|---|---|
| EP | 2 319 874 A1 | * | 5/2011 | .............. C08F 10/00 |
| WO | WO 2005/090418 A1 | * | 9/2005 | ............ C08F 210/16 |

OTHER PUBLICATIONS

Chen, E.Y.X. "Cocatalysts for Metal-Catalyzed Olefin Polymerization: Activators, Activation Processes, and Structure-Activity Relationships", American Chemical Society, Chemical Reviews, 2000, 100, The Dow Chemical Company, Catalysis R&D, Midland, Michigan 48674, pp. 1391-1434.

(Continued)

*Primary Examiner* — Rip A Lee

(57) ABSTRACT

The present invention relates to a A metal complex of formula 1

$$C_y Y M L_j X_n \quad \text{(formula 1)}$$

wherein
Cy is a cyclopentadienyl-type ligand;
M is a metal of group 4;
L is a neutral Lewis basic ligand wherein the number of said neutral ligands "j" is in the range of 0 to the amount that satisfies the 18-electron rule:
X is an anionic ligand; n is an integer denoting the number of anionic ligands X and is 1 or 2, preferably is 2;
Y is a cyclic amidine-containing ligand moiety represented by formula 2

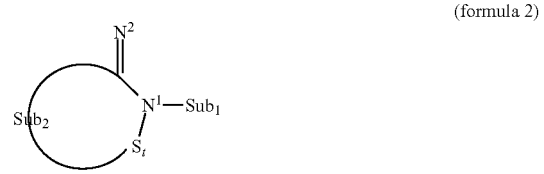

(formula 2)

wherein the amidine-containing ligand is covalently bonded to the metal M via the imine nitrogen atom $N^2$;
S is a —$CH_2$— unit, and t is the integer number denoting the number of S and is in the range of 1-4, more preferably in the range of 1-2, most preferably is 1;
$Sub_1$ is an aliphatic cyclic or linear substituent comprising a group 14 atom through which $Sub_2$ is bonded to the amine nitrogen atom $N^1$;

(Continued)

Sub2 is an optionally substituted C2 unit in which the 2 carbon atoms may be $sp^2$ or $sp^3$ hybridized.

16 Claims, No Drawings

(56) References Cited

U.S. PATENT DOCUMENTS

| | | | | |
|---|---|---|---|---|
| 8,957,170 | B2* | 2/2015 | Van Doremaele | C08F 210/18 |
| | | | | 502/103 |
| 9,546,233 | B2* | 1/2017 | Scott | C07F 17/00 |
| 2009/0012246 | A1 | 1/2009 | Ijpeij et al. | |
| 2013/0066028 | A1* | 3/2013 | Van Doremaele | C08F 210/18 |
| | | | | 526/170 |
| 2013/0131294 | A1* | 5/2013 | Hagadorn | C08F 210/16 |
| | | | | 526/170 |
| 2016/0244543 | A1* | 8/2016 | Berthoud | C08F 210/06 |

OTHER PUBLICATIONS

International Search Report from co-pending Application PCT/EP2015/051571, dated Jul. 1992, reprint Jan. 2004, 2 pages.

\* cited by examiner

METAL COMPLEX WITH A CYCLIC AMIDINE LIGAND

The present invention relates to a metal complex containing a cyclic amidine ligand, a process for its preparation, a catalyst system containing said metal complex, a process for manufacturing polymers wherein said catalyst or catalyst system is used and polymers obtained by this process.

A process for the polymerization of at least one olefin having 2 to 8 carbon atoms in the presence of a polymerization catalyst component comprising an amidine ligand an activator, and optionally a scavenger is known from WO2005090418. WO2005090418 discloses a process for the copolymerization of ethylene and at least one additional alpha olefin having from 3 to 8 carbon atoms, characterized in that said process is a catalyst system for olefin polymerization comprising an organometallic complex of a group 4 metal comprising an amidine ligand; and an activator. WO2005090418 discloses also a process for the copolymerisation of ethylene, alpha olefin and one or more non conjugated dienes.

A disadvantage of this known process is the relatively low affinity of the catalyst to α-olefins and polyenes such as non-conjugated dienes. In addition catalysts employed in this process show limited capability to produce high molecular weight polymers.

The aim of the present invention was to provide a new class of catalyst components that are able to provide higher molecular weight polymers even at elevated temperatures. This aim is achieved by the metal complex according to formula 1

$$C_y Y M L_j X_n \quad \text{(Formula 1)}$$

wherein
Cy is a cyclopentadienyl-type ligand;
M is a metal of group 4;
L is a neutral Lewis basic ligand wherein the number of said neutral ligands "j" is in the range of 0 to the amount that satisfies the 18-electron role;
X is an anionic ligand; n is an integer denoting the number of anionic ligands X and is 1 or 2, preferably is 2;
Y is a cyclic amidine-containing ligand moiety represented by formula 2

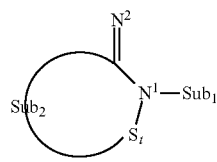

(formula 2)

wherein the amidine-containing ligand is covalently bended to the metal M via the imine nitrogen atom $N^2$;
S is a —$CH_2$— unit, and t is the integer number denoting the number of S and is in the range of 1-4, more preferably in the range of 1-2, most preferably is 1;
Sub1 is an aliphatic cyclic or linear substituent comprising a group 14 atom through which
Sub1 is bonded to the amine nitrogen atom $N^1$;
Sub2 is an optionally substituted C2 unit in which the 2 carbon atoms may be $sp^2$ or $sp^3$ hybridized.

Y

A preferred embodiment of the invention relates to a metal complex of formula 1 wherein Sub1 is an alkyl, alkenyl or alkynyl residue with 1 to 20 carbon atoms, unsubstituted or substituted with halogen, amido, silyl or aryl radicals. Examples for such Sub1 are methyl, n-propyl, i-propyl, tert-butyl, pentyl, cyclopentyl, hexyl, cyclohexyl, heptyl, cycloheptyl, octyl, cyclooctyl, cyclododecyl, octadecyl, adamantly, 1-butenyl, 2-butenyl and propenyl.

A preferred embodiment of the invention relates to a metal complex of formula 1 wherein Y has the general formula 2a

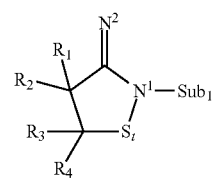

(formula 2a)

wherein $R_1$-$R_4$ are the same or different and each represents a hydrogen atom, a halogen atom, an optionally substituted C1-10 alkyl group or an optionally substituted C1-10 alkoxy group,
or the general formula 2b

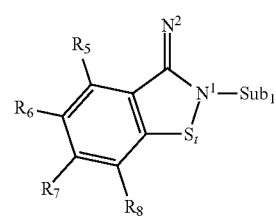

(formula 2b)

wherein $R_5$-$R_8$ are the same or different and each represents a hydrogen atom, a halogen atom, an optionally substituted C1-10 alkyl group, an optionally substituted C1-10 alkoxy group, or the adjacent $R_5$-$R_8$ may be linked to form an aromatic ring optionally substituted. Typical examples (or preferred R5-$R_8$ are hydrogen and fluorine.

In a preferred embodiment, in which Y has the general form 2a with $R_1$-$R_4$ each representing a hydrogen atom or 2b with $R_5$-$R_8$ each representing a hydrogen atom or $R_5$ being a fluorine atom and with Sub1 being methyl, n-propyl, i-propyl, tert-butyl, pentyl, cyclopentyl, hexyl, cyclohexyl, heptyl, cycloheptyl, octyl, cyctooctyl, cyclododecyl, octadecyl, adamantyl, 1-butenyl, 2-butenyl or propenyl, and t is 1.

M

In a preferred embodiment the metal M of group 4 is titanium (Ti), zirconium (Zr) or hafnium (Hf), most preferably titanium.

Cy

A preferred cyclopentadienyl-type ligand is mono or polysubstituted wherein the substituents are selected from the group consisting of halogen, substituted or substituted hydrocarbyl, substituted or unsubstituted hydrocarbyloxy, substituted or unsubstituted silyl and substituted or unsubstituted germyl residues as well as amido and phosphide radicals. Possible substituents are halogen, amido, phosphido, alkoxy, or aryloxy residues. As used herein, the term substituted cyclopentadienyl-type ligand is meant to broadly convey its conventional meaning, namely a substituted ligand having a five-membered carbon ring which is bonded to the metal via a π-type bonding usually in adopting $\eta^5$-coordination to the metal.

Thus, the term cyclopentadienyl-type includes cyclopentadienyl, indenyl and fluorenyl. The term mono- or polysubstituded refers to the fact that one or more aromatic hydrogen atoms of the cyclopentadienyl-type structure have been replaced by one or more other residues. The number of substituents is preferably between 1 and 5 for the cyclopentadienyl ligand, preferably 1 to 7 for the indenyl ligand and 1 to 9 for the fluorenyl ligand.

An exemplary list of substituents for a cyclopentadienyl ligand includes the following groups. For halogen F, Cl and Br may be mentioned.

For substituted or unsubstituted hydrocarbyl radicals are preferred including $C_1$-$C_{20}$ linear and branched alkyl radicals such as methyl, ethyl, propyl, butyl, pentyl, hexyl, heptyl, octyl, nonyl, and decyl, $C_1$-$C_{20}$ hydrocarbyl-substituted and unsubstituted cyclic aliphatic and polycystic aliphatic radicals such as cyclopropyl, cyclobutyl, cyclopentyl, cyclohexyl, phenylcyclohexyl, methylcyclohexyl, cycloheptyl, cyclooctyl, cyclodecyl, cyclododecyl, isopropyldodecyl, adamantyl, norbornyl, tricyclo[5.2.1.0]decyl; $C_1$-$C_{20}$ hydrocarbyl-substituted and unsubstituted aryl radicals including phenyl, methylphenyl, trimethylphenyl, cyctohexylphenyl, napthyl, butylphenyl, butyldimethylphenyl; C1-20 substituted hydrocarbyl radicals including benzyl, N,N-dimethylaminobenzyl, N,N-dimethylaminomethyl, methoxymethyl, diphenylphosphinomethyl, fluorophenyl, trifluoromethylphenyl, fluoromethyl and cyanoethyl.

The preferred substituted or unsubstituted silyl and substituted or unsubstituted germyl residues include Si—$(R^6)_3$ wherein each $R^6$ is selected from the group consisting of hydrogen, $C_{1-8}$ alkyl or alkoxy radical, $C_{6-10}$ aryl or aryloxy, in particular tris(trifluoromethyl)siiyl or tris(perfluorophenyl)silyl, and germyl radicals of the formula —Ge—$(R^7)_3$ wherein each $R^7$ is selected from the group consisting of hydrogen, $C_{1-8}$ alkyl or alkoxy radical, $C_{6-10}$ aryl or aryloxy radical like tris(trifluoromethyl)gerrnyl, or tris(perfluorophenyl)germyl.

The preferred substituted or unsubstituted hydrocarbyloxy radicals include methoxy, ethoxy, butoxy, phenoxy, methylthio, ethylthio and phenylthio.

The preferred amide and phosphide radicals include an amido which is unsubstituted or substituted by up to two $C_{1-8}$ alkyl radicals, and a phosphide radical which is unsubstituted or substituted by up to two $C_{1-8}$ alkyl radicals, In a preferred embodiment the cyclopentadienyl ligand is penta substituted by methyl groups and in consequence Cy is 1,2,3,4,5-pentamethyl-cyclopentadienyl, $C_5Me_5$, commonly referred to as Cp*. Also preferred ligands Cy are other unsubstituted or substituted cyclopentadienyl groups, substituted or unsubstituted indenyl groups, substituted or unsubstituted fluorenyl groups, substituted or unsubstituted tetrahydroindenyl groups, substituted or unsubstituted tetrahydrofluorenyl groups, substituted or unsubstituted octahydrofluorenyl groups, substituted or unsubstituted benzoindanyl groups, substituted or unsubstituted teterocyclopentadienyl groups, substituted or unsubstituted heteroindenyl groups, substituted or unsubstituted heterofluorenyl groups, or their isomers.

L

Preferred is a metal complex of the formula 1 wherein L is an ether, a thioether, an amine, a tertiary phosphane, an inline, a nitrile, an isonitrile, or a bi or oligodentate donor. If more than one ligand L is present they may have different meanings.

The number "j" of neutral ligands in the metal complex of formula 1 may range from 0 to the amount that satisfies the 18-electron rule, as known in the art. Preferably from 0 to 2.

Suitable ethers are diethyl ether, dipropyl ether, diisopropyl ether, dibutyl ether, dihexyl ether, anisole, phenetole, butyl phenyl ether, methoxytoluene, benzyl ethyl ether, diphenyl ether, dibenzyl ether, veratrole, 2-epoxypropane, dioxane, trioxane, furan, 2,5-dimethylfuran, tetrahydrofuran, tetrahydropyrane, 1,2-diethoxyethane, 1,2-dibutoxyethane, and crown ethers. Suitable thioethers are dimethyl sulfide, diethyl sulfide, thiophene, and tetrahydrothiophene. Suitable amines such as methylamine, dimethylamine, trimethylamine, ethylamine, diethylamine, triethylamine, propylamine, diisopropylamine, butylamine, isobutylamine, dibutylamine, tributylamine, pentylamine, dipentylamine, tripentylamine, 2-ethylhexylamine, allylamine, aniline, N-methylaniline, N,N-dimethylaniline, N,N-diethylaniline, toluidine, cyclohexylamine, dicyclohexylamine, pyrrole, piperidine, pyridine, picoline, 2,4-lutidine, 2,6-lutidine, 2,6-di(-butyl) pyridine, quinoline, and isoquinoline, preferably tertiary amines such as trialkylamines, pyridine, bipyridine, tetramethylethylenediamine (TMEDA), and (−)-sparteine). Suitable tertiary phosphanes are triphenylphoshine and trialkylphosphanes. Suitable of imines are ketimines, guanidines, iminoimidazolidines, phosphinimines and amidines. Suitable bidentate ligands are diimines, alkyl or aryldiphoshanes, dimethoxyethane. Suitable oligodentate ligands are triimines (such as tris(pyrazolyl)alkanes), cyclic multidentate ligands comprising heteroatoms of group 13-17, including crown ethers optionally having heteroatoms of group 13-17, azo-crown ethers optionally having heteroatoms of group 13-17, phospha-crown ethers optionally having heteroatoms of group 13-17, crown ethers having combinations of heteroatoms of group 15-18 optionally having heteroatoms of group 13-17 and crown ethers containing heteroatoms of group 14-17 or combinations thereof.

Suitable nitriles are those of the formula, $R^{a)}C\equiv N$, where $R^{a)}$ is individually selected from the group of aliphatic hydrocarbyl, halogenated aliphatic hydrocarbyl, aromatic hydrocarbyl and halogenated aromatic hydrocarbonyl residues. Preferred nitriles are acetonitrile, acrylonitrile, cyclohexanedintirile, benzonitrile, pentafluorbenzonitrile, 2,6-difluorobenzonitrile, 2,6-chlorobenzonitrile, 2,6-dibromobenzonitrile, 4-fluoro-2-trifluoromethyl benzonitrile and 3-pyridinecarbonitrile.

Suitable isonitriles are those of the formula, $R^{b)}N\equiv C$, where $R^{b)}$ is individually selected from the group of aliphatic hydrocarbyl, halogenated aliphatic hydrocarbyl, aromatic hydrocarbyl and halogenated aromatic hydrocarbonyl residues. Preferred isonitriles are tert-butyl isocyanide ($^tBuNC$), ethyl isocyanoacetate, p-toluenesulfonylmethyl isocyanide and cyclohexyl isocyanide preferably tert-butyl isonitrile ($^tBuNC$).

X

Preferred is a metal complex of the formula 1 wherein X means a halogen atom, a C1-10 alkyl group, a C7-20 aralkyl group, a C6-20 aryl group or a C1-20 hydrocarbon-substituted amino group, and more preferably, a halogen atom and a 01-10 hydro-carbon-substituted amino group, most preferably Cl, F, Br, methyl, benzyl, methyl-trimethylsilyl, phenyl, methoxyphenyl, dimethoxyphenyl, N,N-dimethylamino-phenyl, bis dimethylamino)phenyl, fluorophenyl, difluorophenyl, trifluorophenyl, tetrafluoro-phenyl, perfluorophenyl, trialkylsilylphenyl, bis(trialkylsilyl)phenyl and tris(trialkylsilyl)-phenyl. Most preferred are Cl or methyl. In case of more than one X the given meanings are independently.

n

The number of anionic ligands X is denoted as n and depends on the valency of the metal and the valency of the anionic ligand. The preferred catalyst metals are Group 4 metals in their highest oxidation state (i.e. 4+) and the preferred anionic ligands X are monoanionic (such as a halogen or a hydrocarbyl group—especially methyl and benzyl), in some Instances, the metal of the catalyst component may not be in the highest oxidation state. For example, a titanium (III) component would contain only one anionic ligand and a titanium (IV) component would contain 2 anionic ligands X. Preferably n means 2.

Process

The invention further relates to a process for the manufacturing of a metal complex of formula 1 according to the present invention wherein a metal complex of the formula 3

     (formula 3)

in which the radicals Cy, M, L X, J and n have the above given meanings, is reacted with YH or YH-HHal the hydrohalogen acid salt of YH, wherein Y is a cyclic amidine-containing ligand moiety represented by formula 2 and Hal is halogen, in particular F, Cl or Br.

YH or the hydrohalogen acid salt of YH is preferably derived from an aliphatic primary amine $H_2N^1$-Sub1 wherein Sub1 and $N^1$ have the above given meanings which is reacted with the compound of formula 4

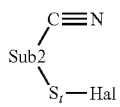     (formula 4)

wherein Sub2, S and t have the above given meanings. Preferably the compound of formula 4 is dissolved in a suitable solvent or without solvent at ambient pressure, preferably at 0.9 bar to 1.1 bar and a temperature in the range of −100 to 100° C.

The addition of the aliphatic primary amine $H_2N^1$-Sub1 is preferably carried out stepwise. The molar ratio of aliphatic primary amine $H_2N^1$-Sub1 to the compound of formula 4 is preferably in the range of 1.8 to 0.8. The reaction is preferably run in the absence of moisture. Preferably, the reaction is carried out under an atmosphere of a dry, inert gas such as nitrogen. Preferably, the reaction is performed at a temperature in the range of −10 to 150° C. Suitable solvents include aliphatic and aromatic hydrocarbon solvents. The hydrohalogen acid salt of YH may be isolated using techniques well known to those skilled in the art by removal of volatiles under reduced pressure or by crystallisation with subsequent removal of the mother liquor by filtration.

To obtain a metal complex of the formula 1 wherein X means a halogen atom, YH or preferably the hydrohalogen acid salt of YH is added to metal complex of the formula 3 wherein X means a halogen atom in a suitable solvent, in the presence of suitable base. The hydrohalogen acid salt of YH is preferably YH.HBr wherein Y has the above given meaning. The hydrohalogen acid salt of YH is preferably neutralized to be in the form of YH wherein Y has the above given meaning by using techniques well known to those skilled in the art. Suitable bases Include organic bases, inorganic bases, and organometallics. Typical example for suitable base is triethylamine and methyl magnesium bromide. The reaction of hydrohalogen acid salt of YH with metal complex of the formula 3 is preferably done in a suitable solvent at ambient pressure, preferably at 0.9 bar to 1.1 bar and a temperature in the range of 0 to 90° C. More preferably, in the range 40 to 80° C. The molar ratio of ligand of formula 2 to metal complex of formula 3 is preferably in the range of 0.8 to 1.5, most preferably the ratio is 0.95 to 1.050. The molar ratio of suitable base to formula 2 or formula 3 is preferably in the range of 1.0 to 5.0, more preferably the ratio is 2 to 4. The metal complex of formula 1 wherein X means a halogen atom may be isolated using techniques well known to those skilled in the art by removal of volatiles under reduced pressure or by crystallisation with subsequent removal of the mother liquor by filtration or by decantation.

Techniques well known to those skilled in the art are used to obtain further a metal complex of the formula 1 wherein X means a C1-10 alkyl group, a C7-20 aralkyl group, a C6-20 aryl group or a C1-20 hydrocarbon-substituted amino group from the metal complex of formula 1 wherein X means a halogen atom by using suitable reagents for the substitution reaction. Preferably, grignard reagents or organolithium reagents are used. More preferably is methyl magnesium chloride or methyl lithium used.

The invention further provides a catalyst system comprising
   a) a metal complex of the formula (1) according to the present invention and
   b) a scavenger.

The preferred metal complex of compound a) is mentioned above. A scavenger is a compound that reacts with impurities present in the process of the invention, which are poisonous to the catalyst, In a preferred embodiment of the present invention the scavenger b) as of the catalyst system is a hydrocarbyl of a metal or metalloid of group 1-13 or its reaction products with at least one sterically hindered compound containing a group 15 or 16 atom.

Preferably, the group 15 or 16 atom of the sterically hindered compound bears a proton. Examples of these sterically hindered compounds are tert-butanol, iso-propanol, triphenylcarbinol, 2,6-di-tert-butylphenol, 4-methyl-2,8-di-tert-butylphenol, 4-ethyl2,6-di-tert-butylphenol, 2,6-di-tert-butylanilin, 4-methyl-2,6-di-tert-butylanilin, 4-ethyl-2,6-di-tert-butylanilin, HMDS (hexamethyldisilazane), diisopropylamine, di-tert-butylamine, diphenylamine and the like. Some non-limiting examples of scavengers are butyllithium including its isomers, dihydrocarbylmagnesium, and hydrocarbylzinc and their reaction products with a sterically hindered compound or an acid, such as HF, HCl, HBr, Hl. Furthermore organoaluminium compounds (E) as defined below can be used as Scavenger b), in particular hydrocarbylaluminoxanes like isobutylaluminoxane (BAO).

The catalyst system of the present invention may in addition contain an activator which differs from the used scavenger.

Activators for single-site catalysts are fairly well known in the art. These activators often comprise a group 13 atom, such as boron or aluminium. Examples of these activators are described in *Chem. Rev.*, 2000, 100, 1391 by E. Y-X. Chen and T. J. Marks. A preferred activator is a borane (C1), a borate (C2, C3) or an organoalumonum compound (E) like alkylaluminoxane such as methyl alurninoxane (MAO). The co-catalyst for activation preferably is any boron compound of the following (C1) to (C3) and/or an organoaluminum compound (E). The organoaluminum compound (E) may be employed as a scavenger and/or a co-catalyst.

(C1) A boron compound represented by the general formula $BQ_1Q_2Q_3$ (C2) A boron compound represented by the general formula $G(BQ_1Q_2Q_3Q_4)$ (C3) A boron compound represented by the general formula (J-H)(BQ$_1$Q$_2$Q$_3$Q$_4$)
(wherein, B is a boron atom in the trivalent valence state, Q$_1$ to Q$_3$ have the same meaning as already mentioned above and Q$_4$ has the same meaning as one of the radicals Q$_1$ to Q$_3$ and Q$_1$ to Q$_4$ may be the same or different. G is an inorganic or organic cation, J is a neutral Lewis base, and (J-H) is a Bronsted acid.

In the boron compound (C1) represented by the general formula BQ$_1$Q$_2$Q$_3$, B is a boron atom in the trivalent valence state, Q$_1$ to Q$_3$ have the above mentioned meanings and may be the same or different.

Specific examples of the compound (C1) include tris (pentafluorophenyl)boranes tris(2,3,5,6-tetrafluorophenyl) borane, tris(2,3,4-tetrafluorophenyl)borane, tris(3,4,5-trifluorophenyl)borane, tris(2,3,4-trifluorophenyl)borane, phenyl-bis(pentafluoro-phenyl)borane and the like, and tris (pentafluorophenyl)borane is most preferable.

In the boron compound (C2) represented by the general formula G(BQ$_1$Q$_2$Q$_3$Q$_4$), G* is an inorganic or organic cation, B is a boron atom in the trivalent valence state, and Q$_1$ to Q$_4$ are as defined for Q$_1$ to Q$_3$ in the above-mentioned (C1).

Specific examples of the inorganic cation G in a compound represented by the general formula G(BQ$_1$Q$_2$Q$_3$Q$_4$) include a ferrocenium cation, alkyl-substituted ferrocenium cation, silver cation and the like, specific examples of the organic cation G thereof include a triphenylmethyl cation and the like. G is preferably a carbenium cations and particularly preferably a triphenylmethyl cation Examples of (B Q$_1$Q$_2$Q$_3$Q$_4$) include tetrakis(pentafluorophenyl)borate, tetrakis(2,3,5,6-tetrafluorophenyl)borate, tetrakis(2,3,4,5-tetrafluorophenyl)borate, tetrakis(3,4,5-trifluorophenyl)borate, teterakis(2,3,4-trifluorophenyl)borate, phenyltris(pentafluoro-phenyl) borate, tetrakis(3,5-bistrifluoromethylphenyl)borate and the like.

As specific combination of them, ferroceniumtetrakis (pentafluorophenyl)borate, 1,1'-dimethylferroceniumtetrakis(pentafluorophenyl)borate, silvertetrakis(pentafluorophenyl)borate, triphenylmethyltetrakis-(pentafluorophenyl) borate, triphenylmethyl-tetrakis(3,5-bistrifluoromethylphenyl)borate and the like are listed, and triphenyl-methyltetrakis(pentafluorophenyl)borate is most preferable.

In the boron compound (C3) represented by the general formula (J-H)$^+$(BQ$_1$Q$_2$Q$_3$Q$_4$), J is a neutral Lewis base, (J-H) is a Bronsted acid, B is a boron atom In the trivalent valence state, and Q$_1$ to Q$_4$ are as defined for Q$_1$ to Q$_4$ in the above-mentioned Lewis acid (C1).

Specific examples of the Bronsted acid (J-H)$^+$ in a compound represented by the general formula (J-H) (BQ$_1$Q$_2$Q$_3$Q$_4$) include a trialkyl-substituted ammonium, N,N-dialkylanillinium, dialkylammonium, triaryl phosphonium and the like, and as the (B Q$_1$Q$_2$Q$_3$Q$_4$), the same compounds as described above are listed. As specific combination of them, there are listed triethylammoniumtetrakis (pentafluoro-phenyl)-borate, tripropylammoniumtetrakis (pentafluorophenyl)borate, tri(n-butyl)ammonium-tetrakis (pentafluorophenyl)borate, tri(n-butyl)ammoniumtetrakis(3, 5-bistrifluoromethyl-phenyl)borate, N(N-dimethyl-aniliniumtetrakis(pentafluoro-phenyl)borate, N,N-diethyl-aniliniumtetrakis(penta-fluorophenyl)borate, N,N2,4,6-pentamethylanilinium-tetrakis-(pentafluoropbenyl)borate, N,N-dimethylaniliniumtetrakis(3,5-bistrifluoromethyl-phenyl)borate, diisopropyl-ammoniumtetrakis(pentafluorophenyl)borate, dicyclohexyl-ammoniumtetrakis-(pentafluorophenyl)borate, triphenylphosphoniumtetrakis(pentafluorophenyl)borate, tri(methylphenyl)phosphoniumtetrakis (pentafluorophenyl)borate, tri(dimethylphenyl)-phosphoniumtetrakis(pentafluorophenyl)borate and the like, and tri(n-butyl)ammonium-tetrakis(pentafluorophenyl)borate or N,N-dimethylaniliniumtetrakis(pentafluor-phenyl) borate, is most preferable.

The molar ratio of metal complex:activating cocatalyst C1-C3 employed preferably ranges from 1:10 to 1:0, more preferably ranges from 1:5 to 1:0, and most preferably from 1:1 to 1:0.

The organoaluminum compound (E) is an aluminum compound having a carbon-aluminum bond, and one or more of aluminum compounds selected from the following (E1) to (E3) are preferable.

(E1) An organoaluminum compound represented by the general formula T$^1_a$AlZ$_{3-a}$ (E2) A cyclic aluminoxane having a structure represented by the general formula {—Al(T$^2$)-O—}$_b$ (E3) Linear aluminoxane having a structure represented by the general formula T$^3${—Al(T$^3$)-O—}$_c$AlT$^3_2$ (wherein, each of T$^1$, T$^2$ and T$^3$ is hydrocarbon group, and all T$^1$, all T$^2$ and all T$^3$ may be the same or different respectively. Z represents a hydrogen atom or halogen atom, and all Zs may be the same or different, 'a' represents a number satisfying 0<a≤3, 'b' is an integer of 2 or more, and V is an integer of 1 or more.)

The hydrocarbon group in E1, E2 or E3 is preferably a hydrocarbon group having 1 to 8 carbon atoms, and more preferably an alkyl group.

Specific examples of the organoaluminum compound (E1) represented by the general formula T$^1_a$AlZ$_{3-a}$ include trialkylaluminums such as trimethylaluminum, triethyl-aluminum, tripropylaluminum, triisobutylaluminum, trihexylaluminum and the like; dialkylaluminum chlorides such as dimethylaluminum chloride, diethylaluminum chloride, dipropylaluminum chloride, diisobutylaluminum chloride, dihexylaluminum chlorides and the like; alkylaluminum dichlorides such as methylaluminum dichloride, ethylaluminum dichloride, propylaluminum dichloride, isobutylaluminum dichloride, hexylaluminum dichloride and the like; dialkylaluminum hydrides such as dimethylaluminum hydride, diethylaluminum hydride, dipropylaluminum hydride, diisobutylaluminum hydride, dihexylaluminum hydride and the like; and so forth.

The trialkylaluminum is preferable, and triethylaluminum or triisobutylaluminum is more preferable.

Specific examples of cyclic aluminoxane E2 having a structure represented by the general formula {—Al(T$^2$)-O—}$_b$, and the linear aluminoxane E3 having a structure represented by the general formula T$^3${—Al(T$^3$)-O—}$_c$AlT$^3_2$ include alkyl groups such as a methyl group, ethyl group, n-propyl group, isopropyl group, n-butyl group, isobutyl group, n-pentyl group, neopentyl group and the like, b is an integer of 2 or more, c is an integer of 1 or more, Preferably, T$^2$ and T$^3$ represent a methyl group or isobutyl group, and b is 2 to 40 and c is 1 to 40. Most preferably, T$^2$ and T$^3$ represent an isobutyl group and b is 2 to 40 and c is 1 to 40.

The above-described aluminoxane is made by various methods. This method is not particularly restricted, and the aluminoxane may be produced according to a known method. For example, a solution prepared by dissolving a trialkylaluminum (for example, trimethylaluminum and the like) in a suitable organic solvent (benzene, an aliphatic hydrocarbon or the like) is allowed to contact with water to produce aluminoxane. Further, there is exemplified a method in which Ia trialkylaluminum (for example, trimathylaluminum and the like) is allowed to contact with a metal salt containing crystal water (for example, copper sulfate hydrate and the like) to produce aluminoxane, The molar ratio of metal complex (1): scavenger b) employed preferably ranges from 0.1:1000 to 0.1:10, more preferably ranges from 0.1:1000 to 0.1:300, and most preferably from 0.14:600 to 0.14:400.

The catalyst system may contain the metal complex of the present invention as such or as in supported form on a supporting material.

A supporting material is defined as an inorganic or organic compound that does not dissolve in the inert hydrocarbon solvent in which the process of the invention is carried out. Suitable inorganic supports include silica, magnesium halides, such as $MgF_3$, $MgCl_2$, $MgBr_2$, $MgI_2$, zeolites, and alumina. Suitable organic supports include polymers. Some non-limiting examples of polymeric supports are polyolefins such as polystryrene, polypropylene and polyethylene, polycondensates such as polyamides and polyesters and combinations thereof.

The invention also relates to a supported catalyst which comprises a metal complex of the formula (1) on a supporting material and optionally a scavenger and/or activator. Preferred supporting material are mentioned above.

Polymerisation

The invention further provides a process for the polymerization of a polymer by polymerizing at least one olefinic monomer comprising contacting said monomer with a metal complex of formula (1).

The preferred process for polymerization is generally concluded by consulting at least one olefinic monomer with the metal complex of the formula (1) or the catalyst system according to the present invention in the gas phase, in slurry, or in solution in an inert solvent preferable a hydrocarbon solvent. Suitable solvents are in the gas phase, in slurry, or in solution in an inert solvent preferably a hydrocarbon solvent. Suitable solvents are a $C_{5-12}$ hydrocarbon such as pentane, hexane, heptane, octane, isomers and mixtures thereof, cyclohexane, methylcyclohexane, pentamethyl heptane and hydrogenated naphtha. The process of the invention may be conducted at temperatures from 10 to 250° C., depending on the product being made.

An olefinic monomer is understood to be a molecule containing at least one polymerizable double bond.

Suitable olefinic monomers are $C_{2-20}$ olefins. Preferred monomers include ethylene and $C_3$, alpha olefins which are unsubstituted or substituted by up to two $C_{1-6}$ alkyl radicals, $C_{8-12}$ vinyl aromatic monomers which are unsubstituted or substituted by up to two substituents selected from the group consisting of $C_{1-4}$ alkyl radicals, and $C_{4-12}$ straight chained or cyclic hydrocarbyl radicals which are unsubstituted or substituted by a $C_{1-4}$ alkyl radical. Illustrative non-limiting examples of such α-olefins are propylene, 1-butane, 1-pentene, 1-hexene, 1-heptene, 1-octane, 1-nonene, 1-decene, 1-undecene, 1-dodecene, 1-tridecene, 1-tetradacene, 1-pentadecene, 1-hexadecene, 1-heptadecene, 1-octadecene, 1-nonadecene, 1-eicosene, 3-methyl-1-butene, 3-methyl-1-pentene, 3-ethyl-1-pentene, 4-methyl-1-pentene, 4-methyl-1-hexene, 4,4-dimethyl1-hexane, 4,4-dimethyl-1-pentene, 4-ethyl-1-hexene, 3-ethyl-1-hexene, 9-methyl-1-decene, 11-methyl-1-dodecene and 12-ethyl-1-tetradecene. These a-olefins may be used in combination.

The monomer may also be a polyene comprising at feast two double bonds. The doubts bonds may be conjugated or non-conjugated in chains, ring systems or combinations thereof, and they may be endocyclic and/or exocyclic and may have different amounts and types of substituents. This means that the polyene may comprise at least one aliphatic, alicyclic or aromatic group, or combinations thereof.

Suitable polyenes include aliphatic polyenes and alicyclic polyenes. More specifically, aliphatic polyenes can be mentioned, such as 1,4-hexadiene, 3-methyl-1,4-hexadiene, 4-methyl-1,4-hexadiene, 5-methyl-1-hexadiene, 4-ethyl-1,4-hexadiene, 1,5-hexadiene, 3-methyl-1,5-hexadiene, 3,3-dimethyl-1,4-hexadiene, 5-methyl-1,4-heptadien, 5-ethyl-1,4-heptadiene, 5-methyl-1,5-heptadiene, 6-methyl-1,5-heptadiene, 5-ethyl-1,5-heptadiene, 1,6-heptadiene, 1,6-octadiene, 4-methyl-1,4-octadiene, 5-methy-1,4-octadiene, 4-ethyl-1,4-octadiene, 5-ethyl-1,4-octadiene, 5-methyl-1,5-octadiene, 6-methyl-1,5-octadiene, 5-ethyl-1,5-octadiene, 6-ethyl-1,5-octadiene, 1,6-octadiene, 6-methyl-1,6-octadiene, 7-methyl-1,6-octadiene, 6-ethyl-1,6-octadiene, 6-propyl-1,6-octadiene, 6-butyl-1,6-octadiene, 1,7-octadiene, 4-methyl-1,4-nonadiene, 5-methyl-1,4-nonadiene, 4-ethyl-1,4-nonadiene, 5-ethyl-1,4-nonadiene, 5-methyl-1,5-nonadiene, 6-methyl-1,5-nonadiene, 5-ethyl-1,5-nonadiene, 6-ethyl-1,5-nonadiene, 6-methyl-1,6-nonadiene, 7-methyl-1,6-nonadiene, 6-ethyl-1,6-nonadiene, 7-ethyl-1,6-nonadiene, 7-methyl-1,7-nonadiene, 8-methyl-1,7-nonadiene, 7-ethyl-1,7-nonadiene, 1,8-nonadiene, 5-methyl-1,4-decadiene, 5-ethyl-1,4-decadiene, 5-methyl-1,5-decadiene, 6-methyl-1,5-decadiene, 5-ethyl-1,5-decadiene, 6-ethyl-1,5-decadiene, 6-methyl-1,6-decadiene, 6-ethyl-1,6-decadiene, 7-methyl-1,6-decadiene, 7-ethyl-1,6-decadiene, 7-methyl-1,7-decadiene, 8-methyl-1,7-decadiene, 7-ethyl-1,7-decadiene, 8-ethyl-1,7-decadiene, 8-methyl-1,8-decadiene, 9-methyl-1,8-decadiene, 8-ethyl-1,8-decadiene, 1,9-decadiene, 1,5,9-decatriene, 6-methyl-1,6-undecadiene, 9-methyl-1,8-undecadiene and 1,13-tetradecadiene, 1,3-butadiene, isoprene.

Alicyclic polyenes may consist of at least one cyclic fragment. Examples of these alicyclic polyenes are vinylcyclohexane, vinylnorbornene, ethylidene norbornene, dicyclopentadiene, cyclooctadiene, 2,5-norbornadiene, 1,4-divinylcyclohexane, 1,3-divinylcyclohexane, 1,3-divinylcyclopentane, 1,5-divinylcyclooctane, 1-allyl-4-vinylcyclo-hexane, 1,4-diallylcyclohexane, 1-allyl-5-vinylcyclooocatane, 1,5-diallylcyclooctane, 1-allyl-4-isopropenylcyclohexane, 1-isopropenyl-4-vinylcyclohaxane and 1-isopropenyl-3-vinylcyclopentane, and 1,4-cyclohexadiene. Preferred polyenes are polyenes having at least one endocyclic double bond and optionally at least one oxocyclic double bond, such as 5-methylene-2-norbornene and 5-ethylidene-2-norbornene, 5-vinylnorbornene, and 2,5-norbornadiene, dicyclopentadiene (DCPD) and vinylcyclohexene.

Examples of aromatic polyenes are divinylbenzene (including its isomers), trivinyl-benzene (including its isomers) and vinylisopropenylbenzene (including its isomers).

All of the above-mentioned monomers may be further substituted with at least one group comprising a heferoatom of group 13-17, or combinations thereof.

Homopolymers, copolymers on the basis of 2 or more of the above-mentioned olefinic monomers and also blends thereof can be prepared with the process of the present invention.

In a preferred embodiment copolymers on the basis of ethylene, at least one $C_{3-12}$ alpha olefin, preferably propylene and at least one non-conjugated diene, preferablya diene selected from the group consisting of 5-methylene-2-norbornene 5-ethylidene-2-norbornene, 5-vinylnorbornene, 2,5-norbornadiene, dicyclopentadiene and vinylcyclohexene, preferably from the group consisting of 5-ethylidene- 2-norbornene and 5-vinylnorbornene are made with metal complex of the present invention.

In the process of the invention the affinity to both α-olefins and polyenes such as non-conjugated dienes is significantly higher than in known process.

An additional advantage of the process of the invention is that polymers with extremely high molecular weight can be obtained. These polymers are characterized by intrinsic viscosity (IV) which is preferably in the range of 7.8 to 50 dl/g measured at 135° C. in decahydronaphthalene or by weight average molecular weight (Mw) which is preferably in the range of 700,000 to 2,000,000 g/mol. Preferably the thus obtained polymers do have an intrinsic viscosity (IV) in the range of 7.8 to 12 dl/g measured at 135° C. in decahydronaphthalene and/or a weight average molecular weight (Mw) which is in the range of 700,000 to 1,500,000 g/mol. These polymers with extremely high molecular weight can be normally achieved by the copolymerization reaction at 90° C. When the reaction temperature goes higher, for example, to 120° C., the concentration of polymer in solution can go up to 30 wt %, preferably up to 25 wt %, in particular up to 20 wt % compared to about 14 wt % when the reaction is carried out at 90° C., which means that with the same equipment almost 30 wt % more polymers can be produced. Another advantage of the process of the invention is that high molecular weight polymers can be prepared even at elevated temperatures. This is particularly advantageous in a process for the preparation of an ethylene/α-olefin polyene copolymer or an ethylene/α-olefin/non-conjugated polyene terpolymer.

The invention further relates to polymers obtainable with the metal complex of the present invention or the catalyst system of the present invention. These obtained polymers preferably have a weight average molecular weight and IV respectively as mentioned above.

Below, the invention will be elucidated on the basis of the following examples and comparative experiments, without being limited thereto.

Test Methods.
Size Exclusion Chromatography (SEC) Coupled to Refractive Index (RI) and Differential Viscometry (DV) Detection
Equipment: PL220 (Polymer Laboratories) SEC with PL220
  DRI concentration detector and
  Viscotek 220R viscometry detector.
  Detectors are operated in parallel configuration.
  Degasser: PL-DG 802
Data processing: Viscotek data processing software, TriSEC
  2.7 or higher version
Columns: PLgel Olexis (4×)
Calibration: Universal calibration with linear polyethylene
  (PE) standard (molecular weight 0.4-4000 kg/mol)
Temperature: 160° C.
Flow: 1.0 ml/min
Injection volume: 0.300 ml
Solvent/eluent: Distilled 1,2,4-trichlorobenzene with about
  1 g/l of Ionol stabilizer
Sample preparation: Dissolving for 4 hours at approx. 150° C.
  Filtration through 1.2 micron Ag filter
  Sample concentration approx. 1.0 mg/ml
  Intrinsic Viscosity (IV) was measured at 135° C. in decahydronaphthalene as solvent,
Fourier transformation infrared spectroscopy (FT-IR), was used to determine the composition of the copolymers according to the method that is known in the art. The FT-IR measurement gives the composition of the various monomers in weight per cents relative to the total composition.

NMR ($^1$H, 300 MHz, $^{13}$C 75.7 MHz, and $^{19}$F at 282 MHz) spectra were measures on a Bruker Avance 300 spectrometer.

Part I: Synthesis of Ligands and Compounds:
General.

All experiments were carried out under nitrogen using Schlenk line techniques. Toluene, hexane and dichloromethane were provided by solvent purification system Braun SPS-800. All other reagents were used as received without further purification.

Synthesis of Compounds for the Comparative Experiments

Synthesis of Me$_5$CpTiCl$_2$(NC(Ph)(iPr$_2$N)) (Compound A)

Me$_5$CpTiCl$_2$(NC(Ph)(iPr$_2$N)) was prepared as described for compound 6 in WO 2005/090418.

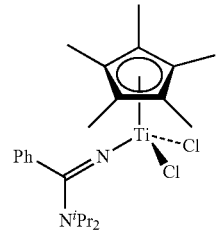

Synthesis of Me$_5$CpTiCl$_2$(NC(Ph)(iPr$_2$N)) (Compound AM)

To a stirring toluene (15 mL) solution of Cp*Ti(NC(Ph)N$^i$Pr$_2$)Cl$_2$ (3) (1.00 g, 2.20 mmol) was added dropwise MeLi (2.80 ml, 1.6 M in Et$_2$O, 4.0 mmol) and the resulting solution was stirred for 16 h. The volatiles were then removed in vacuo and the yellow solid was then extracted into n-hexanes (50 ml), Concentration of the solution to ca, 15 ml and subsequent storage at −30° C. for 24 h resulted in crystallisation of the desired product as large yellow crystals which were isolated and dried in vacuo. Yield=0.37 g (40%). The product was characterized by $^1$H-NMR and $^{13}$C-NMR.

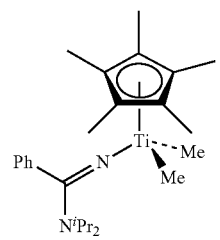

Synthesis of Me$_5$CpTiCl$_2$(NC(Ph)(2,6-Me$_2$PhN) (Compound B)

Me$_5$CpTiCl$_2$(NC(Ph)(2,6-Me$_2$PhN) was prepared as described for compound 11 in WO 2005/090418.

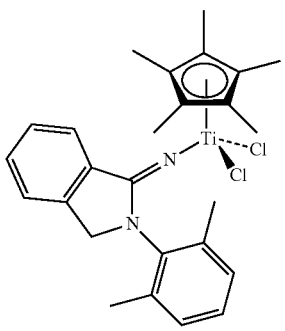

Chemical Formula: $C_{26}H_{30}Cl_2N_2Ti$
Molecular Weight: 489.30

Synthesis of Me$_5$CpTiCl$_2$(NC(Ph)(2,6-Me$_2$PhN) (Compound BM)

To a solution of Compound B (2.02 g, 4.14 mmol) in toluene (150 ml) was added methyl magnesium chloride solution (3M in THF, 3.08 mL, 9.24 mmol) dropwise at −80° C., Mixture was allowed to warm to room temperature and stirred overnight. The mixture was concentrated and hexane was added (50 ml). It was filtered off and mixture was concentrated to approx. 20 ml. Solution was stored at −80° C. After 24 h remaining liquid was removed by decantation and resulting solid was dried under reduced pressure to yield the product as a yellow powder (0.833 g, 1.86 mmol, 45%), The powder was characterized by $^1$H NMR (300 MHz) (C$_6$D$_6$) δ (ppm): 8.08-6.79 (m, 7H); 4.12 (s, 2H); 2.18 (s, 6H); 1.89 (s, 15H); 0.48 (s, 6H) and $^{13}$C NMR (75 MHz) (C$_6$D$_6$) δ (ppm):141.9; 138.4; 138.0; 136.7; 130.8; 128.8; 128.8; 128.2; 124.6; 123.3; 120.6; 52.5; 47.3; 18.8; 12.4.

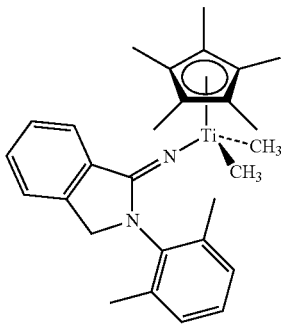

Chemical Formula: $C_{28}H_{36}N_2Ti$
Molecular Weight: 448.47

Synthesis of Me$_5$CpTiCl$_2$(NC(Ph)(2,4,6-Me3PhN) (Compound C)

A mixture of 2-(2,4,6-trimethylphenyl)isoindolin-1-imine hydrobromide (2.00 g, 6.04 mmol) and pentamethylcyclopentadienyl titanium trichloride (1.748 g, 6.04 mmol) was dissolved in toluene (60 ml) and triethylamine (2.10 mL, 15.1 mmol) was added. If was stirred at 50° C. overnight. If was filtered off and the filtrate was concentrated to approx. 5 ml. Hexane (30 ml) was added and stirred for 20 min. It was filtered off and dried under reduced pressure to yield the product as a yellow solid (1.84 g, 3.68 mmol, 61%).

The powder was characterized by $^1$H NMR (300 MHz) (C$_6$D$_6$) δ (ppm): 2.00 (s, 15H); 2.08 (s, 3H); 2.12 (s, 6H); 3.97 (s, 2H); 8.79 (s, 2H); 6.86 (d, 1H); 7.10 (m, 2H); 8.26 (d, 1H) and $^{13}$C NMR (75 MHz) (C$_6$D$_6$) δ (ppm): 141.2; 137.2; 131.6; 129.7; 129.1; 127.8; 126.1; 123.0; 54.0; 21.4; 18.9; 13.4.

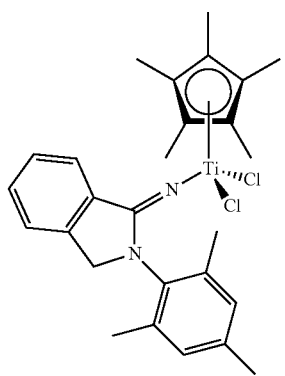

Chemical Formula: $C_{27}H_{32}Cl_2N_2Ti$
Molecular Weight: 503.33

Synthesis of Me$_5$CpTiMe$_2$(NC(Ph)(2,4,6-Me$_3$PhN) (Compound CM)

To a solution of Compound C (503 mg, 1.00 mmol) in toluene (40 ml) was added methyl magnesium chloride solution (3M in THF, 1.00 mL, 3.00 mmol) dropwise at −80° C. Mixture was allowed to warm to room temperature and stirred overnight. Trimethylsilyl chloride (0.150 mL, 1.15 mmol) was added and stirred for 15 min. Volatiles ware removed under reduced pressure and hexane was added (50 mL). It was filtered off and volatiles were removed under reduced pressure to yield the product as a yellow powder (230 mg, 0.497 mmol, 50%).

The powder was characterized by $^1$H NMR (300 MHz) (C$_6$D$_6$) δ (ppm); 0.50 (s, 6H); 1.90 (s, 15H); 2.09 (s, 3H); 2.18 (s, 6H); 4.16 (s, 2H); 6.79 (s, 2H); 8.97 (d, 1H); 7.18 (m, 2H); 7.95 (d, 1H) and $^{13}$C NMR (75 MHz) (C$_6$D$_6$) δ (ppm): 141.8; 137.9; 137.5; 130.8; 129.5; 124.6; 123.3; 120.5; 52.8; 47.2; 21.4; 18.8; 12.4.

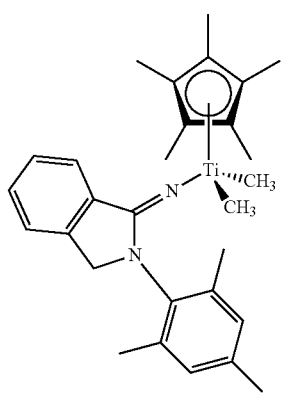

Chemical Formula: $C_{29}H_{36}N_2Ti$
Molecular Weight: 462.49

Synthesis of Compounds for Inventive Examples

Synthesis of the 2-cyclopentylisoindolin-1-imine hydrobromide (Ligand 1)

2-(Bromomethyl)benzonitrile (1.9 g, 10.0 mmol) was dissolved in toluene (20 mL) and cyclopentylamine (0.851 g, 10.0 mmol), dissolved in toluene (10 mL), was added dropwise within 20 min. It was stirred at 50 overnight. The solvent was evaporated to approx. 5 ml and diethylether (40 mL) was added. It was filtered off, washed with diethylether (3×20 ml) and dried under reduced pressure to yield the product as a white solid (1.49 g, 5.30 mmol, 53%).

The powder was characterized by $^1$H NMR (300 MHz) (CDCl$_3$) δ (ppm): 1.58-1.73 (m, 2H); 1.79-1.96 (m, 4H); 2.31-2.44 (m, 2H); 4.69 (s, 2H); 5.21 (m, 1H); 7.53 (d, 1H); 7.63 (m, 2H); 8.93 (d, 1H); 9.65 (s, 1H); 10.18 (s, 1H).

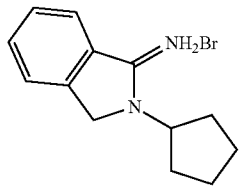

Synthesis of Me$_5$CpTiCl$_2$(NC(Ph)(c-C$_5$H$_9$N) (Compound 1)

A mixture of 2-cyclopentylisoindolin-1-imine hydrobromide (0.500 g, 1.78 mmol) and pentamethylcyclopentadienyl titanium trichloride (0.515 g, 1.78 mmol) was dissolved in toluene (50 ml) and triethylamine (1.30 mL, 9.38 mmol) was added, it was stirred at 50° C. overnight. Toluene (40 ml) was added and the hot solution (70° C.) was filtered off. The filtrate was concentrated to approx. 20 ml and hexane (50 mL) was added and stirred for 20 min. It was filtered off and dried under reduced pressure to yield the product as a yellow solid (0.405 g, 0.836 mmol, 50%).

The powder was characterised by $^1$H NMR (300 MHz) (C$_6$D$_6$) δ (ppm): 1.29-1.69 (8H, m); 2.20 (s, 15H); 3.54 (2H, s); 4.28-4.42 (1H, m); 6.81-6.88 (1H, m); 7.05-7.11 (2H, m); 7.90-7.98 (1H, m).

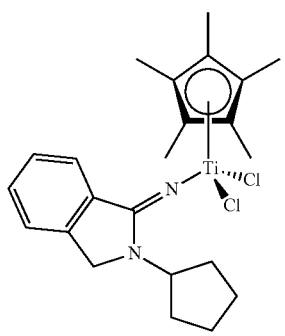

Chemical Formula: C$_{23}$H$_{35}$Cl$_2$N$_2$Ti
Molecular Weight: 458.31

Synthesis of Me$_5$CpTiMe$_2$(NC(Ph)(c-C$_5$H$_9$N) (Compound 1M)

To a solution of Compound 1 (200 mg, 0.440 mmol) in toluene (30 mL) was added methyl magnesium chloride solution (1M in THF, 1.76 mL, 1.78 mmol) dropwise at −80° C. Mixture was allowed to warm to room temperature and stirred overnight. Trimethylsilyl chloride (0.10 ml) was added and stirred for 30 min. The mixture was concentrated and hexane was added (100 ml), it was filtered off and solvent was evaporated to dryness to yield Compound 1M as a yellow solid (60 mg, 31% Yield).

The powder was characterized by $^1$H NMR (300 MHz) (C$_6$D$_6$) δ (ppm): 0.68 (s, 6H); 1.19-1.37 (m, 4H); 1.57 (m, 2H); 1.81 (m, 2H); 2.07 (s, 15H); 3.71 (s, 2H); 4.85 (m, 1H); 6.95 (d, 1H); 7.13 (m, 2H); 7.82 (d, 1H).

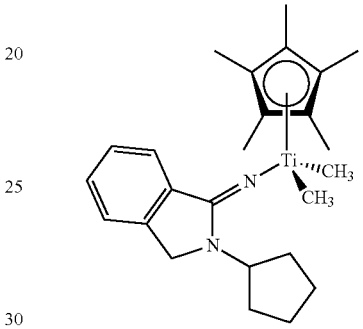

Chemical Formula: C$_{25}$H$_{41}$N$_2$Ti
Molecular Weight: 417.47

Synthesis of the 2-cyclohexylisoindolin-1-imine hydrobromide (Ligand 2)

2-(Bromomethyl)benzonitrile (4.90 g, 25.0 mmol) was dissolved in toluene (10 mL) and cyclohexylamine (2.48 g, 25.0 mmol), dissolved in toluene (10 ml), was added dropwise within 20 min. If was stirred at 50° C. overnight. The solvent was evaporated to approx. 10 ml and diethylether (20 ml) was added. It was filtered off, washed with diethylether (2×20 ml) and dried under reduced pressure to yield the product as a white solid (6.71 g, 22.8 mmol, 91%).

The powder was characterized by $^1$H NMR (300 MHz) (CDCl$_3$) δ (ppm): 1.10-2.14 (10H, m); 4.67 (2H, s); 4.95 (1H, m); 7.51 (1H, d); 7.58-7.68 (2H, m); 9.05 (1H, d); 9.81 (1H, s); 10.25 (1H, s).

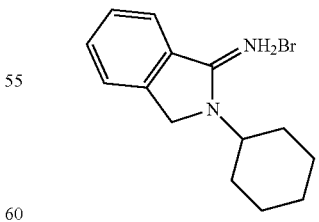

Synthesis of Me$_5$CpTiCl$_2$(NC(Ph)(c-C$_5$H$_{11}$N) (Compound 2)

A mixture of 2-cyclohexylisoindolin-1-imine hydrobromide (2.95 g, 10.0 mmol) and pentamethylcyclopentadienyl titanium trichloride (2.89 g, 10.0 mmol) was dissolved in toluene (50 mL) and triethylamine (3.49 ml, 25.0 mmol) was added. It was stirred at 50° C. overnight. Toluene (40 ml) was added and the hot solution (70° C.) was filtered off. The filtrate was concentrated to approx. 20 mL and hexane (50 mL) was added and stirred for 20 min. It was filtered off and dried dried under reduced pressure to yield the product as a yellow solid (1.53 g, 3.27 mmol, 33%).

The powder was characterized by $^1$H NMR (300 MHz) ($C_6D_6$) δ (ppm): 0.85-1.70 (10H, m); 2.18 (s, 15H); 3.55 (2H, s); 4.15 (1H, m); 6.85 (1H, m); 7.07 (2H, m); 7.90 (1H, m) and $^{13}$C NMR (75 MHz) ($C_6D_6$) δ (ppm): 141.3; 131.2; 127.1; 124.9; 123.0; 53.5; 48.2; 32.0; 26.3; 26.1; 13.6.

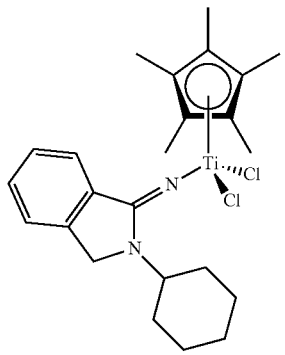

Chemical Formula: $C_{24}H_{37}Cl_2N_2Ti$
Molecular Weight: 472.34

Synthesis of $Me_5CpTiMe_2(NC(Ph)(c-C_5H_{11}N)$ (Compound 2M)

To a solution of Compound 2 (500 mg, 1.07 mmol) in toluene (40 mL) was added methyl magnesium chloride solution (3M in THF, 1.07 mL, 3.21 mmol) dropwise at −80° C. Mixture was allowed to warm to room temperature and stirred overnight. Trimethylsilyl chloride (0.15 ml) was added and stirred for 30 min. The mixture was concentrated and hexane was added (100 mL). It was filtered oft and solvent was evaporated to dryness to yield Compound 2M as a yellow solid (0.35 g, 76% Yield).

The powder was characterized by $^1$H NMR (300 MHz) ($C_6D_6$) δ (ppm): 0.66 (s, 6H); 1.07-1.80 (m, 10H); 2.07 (s, 15H); 3.76 (s, 2H); 4.32 (m, 1H); 6.96 (d, 1H); 7.15 (m, 2H); 7.83 (d, 1H) and $^{13}$C NMR 75 MHz ($C_6D_6$) δ (ppm): 141.8; 130.4; 124.1; 123.1; 120.2; 52.1; 47.5; 45.3; 31.9; 26.7; 26.4; 12.6.

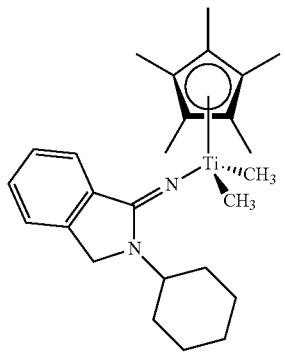

Chemical Formula: $C_{26}H_{43}N_2Ti$
Molecular Weight: 431.50

Synthesis of the 2-cycloheptylisoindolin-1-amine hydrobromide (Ligand 3)

2-(Bromomethyl)benzonitrile (1.96 g, 10.0 mmol) was dissolved in toluene (50 mL) and cycloheptylamine (1.13 g, 10.0 mmol) was added dropwise within 20 min. It was stirred at 50° C. for 5 h. The solvent was removed by decantation, the white solid residue was washed with diethylether (3×15 mL) and dried under reduced pressure overnight to yield the product as a white powder (1.56 g. 5.05 mmol, 51%)

The powder was characterized by $^1$H NMR (300 MHz) ($CDCl_3$) δ (ppm): 1.51-1.98 (m, 10H); 2.15 (m, 2H); 4.89 (s, 2H); 5.09 (m, 1H); 7.52 (d, 1H); 7.63 (m, 2H); 8.98 (d, 1H); 9.77 (s, 1H); 10.28 (s, 1H).

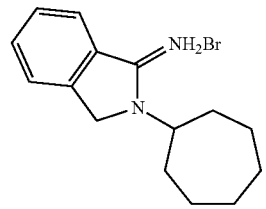

Chemical Formula: $C_{15}H_{21}BrN_2$
Molecular Weight: 309.24

Synthesis of $Me_5CpTiCl_2(NC(Ph)(c-C_7H_{13}N)$ (Compound 3)

A mixture of 2-cycloheptylisoindolin-1-imine hydrobromide (500 mg, 1.62 mmol) and pentamethylcyclopentadienyl titanium trichloride (468 mg, 1.62 mmol) was dissolved in toluene (40 mL) and triethylamine (0.80 mL, 4.33 mmol) was added. It was stirred at 50° C. for 4 h and another portion of triethylamine (0.80 mL, 4.33 mmol) was added. It was stirred at 50° C. for 72 h. The solution was filtered off, the filtrate was concentrated to approx. 5 mL and hexane (40 mL) was added and stirred for 20 min. It was filtered off and dried dried under reduced pressure to yield the product as a yellow solid (303 mg, 0.630 mmol, 39%).

The powder was characterized by $^1$H HUB (300 MHz) ($C_6D_6$) δ (ppm): 1.09-1.68 (m, 12H); 2.19 (s, 15H); 3.55 (s, 2H); 4.28-4.42 (m, 1H); 6.81-6.89 (m, 1H); 7.05-7.11 (m, 2H); 7.10-7.17 (m, 1H).

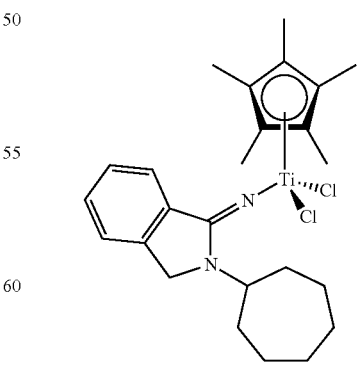

Chemical Formula: $C_{25}H_{34}Cl_2N_2Ti$
Molecular Weight: 481.32

Synthesis of Me$_5$CpTiMe$_2$(NC(Ph)(c-C$_7$H$_{13}$N) (Compound 3M)

To a solution of Compound 3 (200 mg, 0.42 mmol) in toluene (30 ml) was added methyl magnesium chloride solution (1M in THF, 1.66 ml, 1.66 mmol) dropwise at −80° C. Mixture was allowed to warm to room temperature and stirred overnight. Trimethylsilyl chloride (0.10 ml) was added and stirred for 30 mm. The mixture was concentrated and hexane was added (100 ml). It was filtered off and solvent was evaporated to dryness to yield Compound 3M as a yellow solid (110 mg, 0.247 mmol, 59%).

The powder was characterized by $^1$H NMR (300 MHz) (C$_6$D$_6$) δ (ppm): 0.87 (s, 8H); 1.23-1.61 (m, 12H); 2.09 (s, 15H); 3.78 (s, 2H); 4.53 (m, 1H); 6.98 (m, 1H); 7.14 (m, 2H); 7.82 (m, 1H),

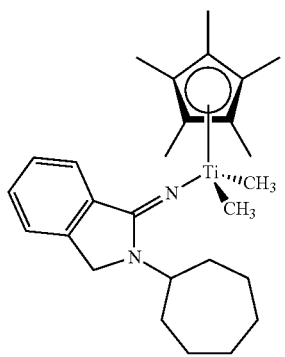

Chemical Formula: C$_{27}$H$_{45}$N$_2$Ti
Molecular Weight: 445.53

Synthesis of the 2-cyclooctylisoindolin-1-imine hydrobromide (Ligand 4)

2-(Bromomethyl)benzonitrile (3.00 g, 15.3 mmol) and cyclooctylamine (1.95 g, 15.3 mmol) were mixed without solvent at room temperature. The reaction was performed at room temperature for 5 min. The resulting dark gel was washed with diethylether (3×20 ml) to yield the product as a white solid (3.72 g, 11.5 mmol, 75%).

The powder was characterized by $^1$H NMR (300 MHz) (CDCl$_3$) δ (ppm): 1.7 (m, 15H); 4.7 (s, 2H); 5 (s, 1H); 7.6 (m, 4H) and $^{13}$C NMR (75 MHz) (CDCl$_3$) δ (ppm): 24.2; 27.4; 31.3; 52.3; 56.9; 126.7; 129.4; 160.8.

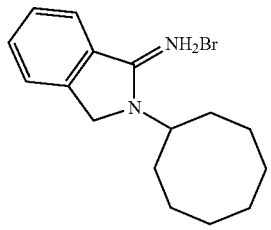

Chemical Formula: C$_{16}$H$_{23}$BrN$_2$
Molecular Weight: 323.27

Synthesis of Me$_5$CpTiCl$_2$(NC(Ph)(c-C$_8$H$_{15}$N) (Compound 4)

To a solution of pentamethylcyclopentadienyl titanium trichloride (1.50 g, 5.30 mmol) and 2-cyclooctylisoindolin-1-imine hydrobromide (1.70 g, 5.30 mmol) in toluene (30 mL) was added triethylamine (2.80 mL, 21.0 mmol). The reaction was heated up to 50° C. and stirred overnight. The solution was filtered off, the filtrate was concentrated to approx. 10 mL. The flask was stored at −20° C. After 2 days remaining liquid was removed by decantation and resulting solid was dried under reduced pressure to yield the product as a bright-yellow powder (2.12 g, 4.24 mmol, 81%).

The powder was characterized by $^1$H NMR (300 MHz) (C$_6$D$_6$) δ (ppm): 1.26-1.89 (m, 14H); 2.30 (s, 15H); 3.68 (s, 2H); 4.53 (s, 1H); 7.02 (m, 1H); 7.20 (m, 2H); 8.07 (m, 1H) and $^{13}$C NMR (75 MHz) (C$_6$D$_6$) δ (ppm): 13.6; 25.4; 26.4; 27.1; 32.6; 48.1; 54.1; 123.0; 125.2; 127.1; 131.2; 135.2; 141.3; 159.9.

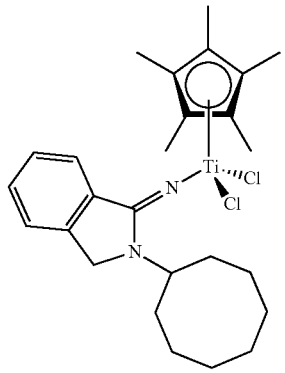

Chemical Formula: C$_{26}$H$_{41}$Cl$_2$N$_2$Ti
Molecular Weight: 500.39

Synthesis of Me$_5$CpTiMe$_2$(NC(Ph)(c-C$_8$H$_{15}$N) (Compound 4M)

To a solution of Compound 4 (400 mg, 0.800 mmol) in toluene (30 ml) was added methyl magnesium chloride solution (3M in Et$_2$O, 0.533 ml, 1.60 mmol) dropwise at −80° C. Mixture was allowed to warm to room temperature and stirred overnight. Hexane was added (15 ml), the resulting suspension was filtered off and solvent was evaporated to dryness to yield Compound 4M as a yellow solid (0.29 g, 0.63 mmol, 78%).

The powder was characterized by $^1$H NMR (300 MHz) (C$_6$D$_6$) δ (ppm): 0.78 (s, 8H); 1.32-1.89 (m, 14H); 2.20 (s, 15H); 3.89 (s, 2H); 4.76 (s, 1H); 7.02 (m, 1H); 7.20 (m, 2H); 8.07 (m, 1H) and NMR (75 MHz) (C$_6$D$_6$) δ (ppm): 12.7; 25.6; 26.5; 27.3; 32.6; 45.6; 47.4; 52.6; 123.0; 125.2; 127.1; 131.2; 135.2; 141.3; 159.9.

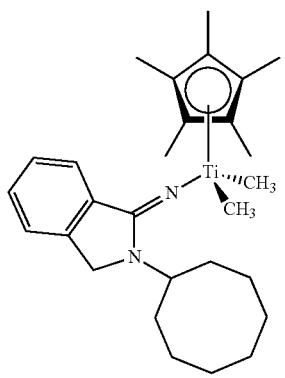

Chemical Formula: C$_{28}$H$_{47}$N$_2$Ti
Molecular Weight: 459.55

Synthesis of the 2-cyclododecylisoindolin-1-imine hydrobromide (Ligand 5)

2-(Bromomethyl)benzonitrile (3.00 g, 15.3 mmol) and cyclododecylamine (2.80 g, 15.3 mmol) were mixed without solvent at room temperature. The reaction was performed at room temperature for 5 min. The resulting dark gel was washed with diethylether (3×20 ml) to yield the product as a white solid (4.40 g, 11.6 mmol, 78%). The powder was characterized by $^1$H NMR (300 MHz) (CDCl$_3$) δ (ppm); 1.38 (m, 22H); 4.75 (s, 2H); 4.98 (s, 1H); 7.80 (m, 3H), 9.02 (d, 1H).

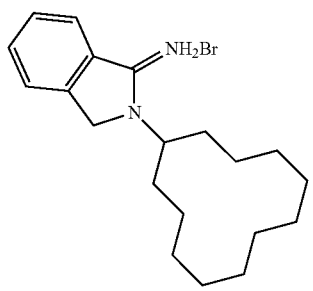

Chemical Formula: C$_{20}$H$_{31}$BrN$_2$
Molecular Weight: 379.38

Synthesis of Me$_5$CpTiCl$_2$(NC(Ph)(c-C$_2$H$_{23}$N) (Compound 5)

To a solution of pentamethylcyclopentadienyl titanium trichloride (1.53 g, 5.27 mmol) and 2-cyclododecylisoindolin-1-imine hydrobromide (2.00 g, 5.27 mmol) in toluene (30 ml) was added triethylamine (2.80 ml, 21.0 mmol). The reaction was heated up to 50° C. and stirred overnight. The solution was filtered off, the filtrate was concentrated to approx. 10 mL. The flask was stored at −80° C. After 2 days remaining liquid was removed by decantation and resulting solid was dried under reduced pressure to yield the product as a yellow powder (2.20 g, 3.95 mmol, 75%).

The powder was characterized by $^1$H NMR (300 MHz) (C$_6$D$_6$) δ (ppm): 1.22-1.78 (m, 22H); 2.31 (s, 15H); 3.76 (s, 2H); 4.5 (m, 1H, (—CH$_2$)$_2$CH—N); 6.98-7.33 (m, 4H) and $^{13}$C NMR (75 MHz) (C$_6$D$_6$) δ (ppm): 13.7; 22.9; 24.2; 24.5; 24.9; 25.2; 29.1; 49.1; 52.3; 122.9; 125.9; 126.0; 127.2; 129.7; 131.2; 141.1; 161.4.

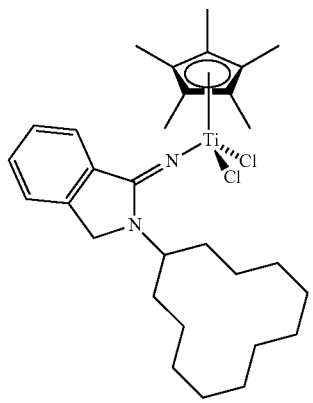

Chemical Formula: C$_{30}$H$_{49}$Cl$_2$N$_2$Ti
Molecular Weight: 556.50

Synthesis of Me$_5$CpTiMe$_2$(NC(Ph)(c-C$_2$H$_{23}$N) (Compound 5M)

To a solution of Compound 5 (400 mg, 0,719 mmol) in toluene (30 mL) was added methyl magnesium chloride solution (3$_M$ in Et$_2$O, 0.473 mL, 1.42 mmol) dropwise at −80° C. Mixture was allowed to warm to room temperature and stirred overnight. A color change from red to orange was observed. Hexane was added (15 ml), the resulting suspension was filtered off and solvent was evaporated to dryness to yield Compound 5M as a yellow solid (0.29 g, 0.56 mmol, 81%).

The powder was characterized by $^1$H NMR (300 MHz) (C$_6$D$_6$) δ (ppm): 0.78 (s, 6H); 1.48-1.70 (m, 22H); 2.19 (s, 15H); 3.95 (s, 2H); 4.81 (m, 1H); 7.12 (m, 1H); 7.27 (m, 2H); 7.86 (m, 1H) and $^{13}$C NMR (75 MHz) (C$_6$D$_6$) δ (ppm): 11.0; 21.5; 22.6; 22.7; 23.1; 23.1; 27.5; 44.7; 46.1; 48.0; 118.5; 121.3; 122.7; 126.5; 128.7; 135.4; 139.7; 156.0.

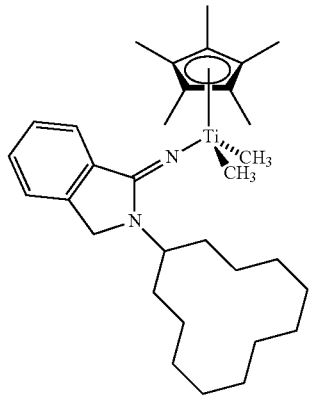

Chemical Formula: C$_{32}$H$_{55}$N$_2$Ti
Molecular Weight: 515.66

Synthesis of the 2-tert-butyl-1-imine hydrobromide (Ligand 6)

2-(Bromomethyl)benzonitrile (4.97 g, 25.4 mmol) was dissolved in toluene (100 mL) and tert-butylamine (2.69 g, 25.4 mmol was added at ambient temperature. It was heated to reflux (bath temperature 115° C.) and stirred for 30 h. Another portion of tert-butylamine (1.62 ml, 15.3 mmol) was added and stirred at reflux for another 30 h. If was filtered off, washed toluene (50 mL) and dried under reduced pressure to yield the product as a light pink solid (5.06 g, 18.8 mmol, 75%).

The powder was characterized by $^1$H NMR (300 MHz) (CDCl$_3$) δ (ppm): 9.07 (d, 1H), 7.91-7.10 (m, 4H), 4.96 (s, 2H), 1.77 (s, 9H) and $^{13}$C NMR (75 MHz) (CDCl$_3$) δ (ppm): 161.0; 140.1; 133.7; 130.4; 129.5; 126.3; 122.5; 58.1; 55.8; 28.53.

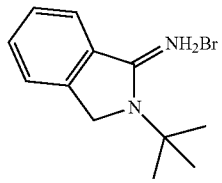

Chemical Formula: C$_{12}$H$_{17}$BrN$_2$
Molecular Weight: 269.18

Synthesis of Me$_5$CpTiCl$_2$(NC(Ph)(c-C$_4$H$_9$N) (Compound 6)

To a solution of pentamethylcyclopentadienyl titanium trichloride (0.891 g, 3.08 mmol) and 2-tert-butyl-1-imine hydrobromide (0.824 g, 3.07 mmol) in toluene (100 ml) was added triethylamine (1.02 ml, 7.36 mmol). The reaction was heated up to 50° C. and for 94 h. The solution was filtered off, the filtrate was concentrated to approx. 10 mL. The flask was stored at −80° C. After 2 days remaining liquid was removed by decantation and resulting solid was dried under reduced pressure to yield the product as a yellow powder (300 mg, 0.672, 22%).

The powder was characterized by $^1$H NMR (300 MHz) (C$_6$D$_6$) δ (ppm): 8.09-6.71 (m, 4H); 3.63 (s, 2H); 2.19 (s, 15H); 1.28 (s, 9H) and $^{13}$C NMR (75 MHz) (C$_6$D$_6$) δ (ppm): 140.2; 137.1; 131.1; 127.3; 125.4; 122.5; 56.7; 51.4; 28.7; 13.6.

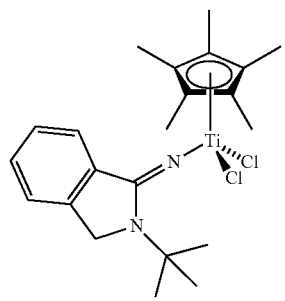

Chemical Formula: C$_{22}$H$_{35}$Cl$_2$N$_2$Ti
Molecular Weight: 446.30

Synthesis of Me$_5$CpTiMe$_2$(NC(Ph)(c-C$_4$H$_9$N) (Compound 6M)

To a solution of Compound 6 (1.00 g, 2.30 mmol) in toluene (40 ml) was added methyl lithium solution (1.6 M in hexanes, 3.10 ml, 5.00 mmol) dropwise at −80° C. A color change to red-orange was observed immediately. Mixture was allowed to warm to room temperature and stirred for 4 h. Trimethylsilyl chloride (0.150 ml, 1.15 mmol) was added and stirred for 15 min. Volatiles were removed under reduced pressure. I was extracted with hexane (3×15 mL), filtered and removal of solvent under reduced pressure to yield the product as a waxy solid (0.58 g, 1.43 mmol, 64%).

The waxy solid was characterized by $^1$H NMR (300 MHz) (C$_6$D$_6$) δ (ppm): 7.61 (m, 1H); 7.19-7.13 (m, 2H); 6.91 (m, 1H); 3.85 (s, 2H); 2.07 (s, 15H); 1.44 (s, 9H), 0.64 (s, 8H) and $^{13}$C NMR (75 MHz) (C$_6$D$_6$) δ (ppm); 158.3; 140.1; 138.1; 130.0; 127.6; 123.6; 122.3; 119.9; 55.2; 50.0; 47.2; 28.1; 12.3.

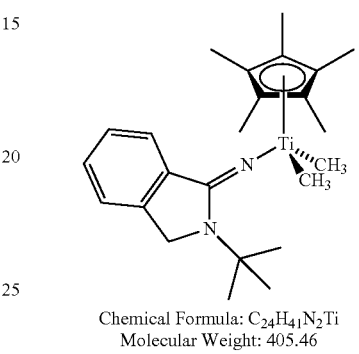

Chemical Formula: C$_{24}$H$_{41}$N$_2$Ti
Molecular Weight: 405.46

Synthesis of the 2-adamantylisoindolin-1-imine hydrobromide (Ligand 7)

2-(Bromomethyl)benzonitrile (2.60 g, 13.3 mmol) was dissolved in toluene (150 ml) and adamantylamine (2.00 g, 13.3 mmol) was added. It was heated to reflux (bath temperature 115° C.) and stirred overnight. It was filtered off to yield the product as a white solid (3.79 g, 10.9 mmol, 82%).

The powder was characterized by $^1$H NMR (300 MHz) (CDCl$_3$) δ (ppm): 1.7 (m, 6H); 2.0 (m, 3H); 2.3 (m, 6H); 5.0 (s, 2H); 7.6 (m, 4H); 8.5 (s, 1H) and $^{13}$C NMR (75 MHz) (CDCl$_3$) δ (ppm): 29.9; 35.77; 39.6; 59.9; 130.4; 140.3; 169.6.

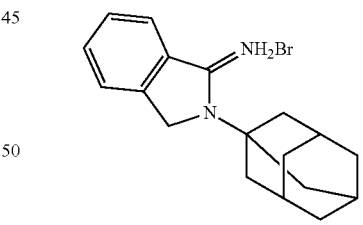

Chemical Formula: C$_{18}$H$_{23}$BrN$_2$
Molecular Weight: 347.29

Synthesis of Me$_5$CpTiCl$_2$(NC(Ph)(AdamantylN) (Compound 7)

To a solution of pentamethylcyclopentadienyl titanium trichloride (1.50 g, 5.20 mmol) and 2-adamantylisoindolin-1-imine hydrobromide (1.80 g, 5.20 mmol) in toluene (30 mL) was added triethylamine (2.80 ml, 21.0 mmol). The reaction was heated up to 50° C. and stirred for 7 d. The solution was filtered off, the filtrate was concentrated to approx. 10 mL. The flask was stored at −80° C. After 3 days remaining liquid was removed by decantation and resulting solid was dried under reduced pressure to yield the product as a yellow powder (191 mg, 0.364 mmol, 7%).

The powder was characterized by $^1$H NMR (300 MHz) (C$_6$D$_6$) δ (ppm): 1.70 (m, 6H); 1.85 (m, 3H); 2.1 (m, 8H); 2.29 ("m", 15H); 3.82 (s, 2H); 7.11-7.33 (m, 4H) and $^{13}$C NMR (75 MHz) (C$_6$D$_6$) δ (ppm): 13.5; 30.5; 36.6; 40.5; 50.4; 58.1; 122.4; 125.5; 127.1; 131.1.

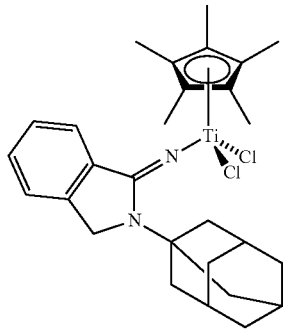

Chemical Formula: C$_{28}$H$_{41}$Cl$_2$N$_2$Ti
Molecular Weight: 524.41

Synthesis of the 2-octadecylisoindolin-1-imine (Ligand 8)

2-Bromomethylbenzonitrile (7.65 g, 39.0 mmol) was dissolved in toluene (50 mL) and octadecylamine (8.09 g, 30 mmol), dissolved in 150 ml of toluene (very bad solubility), is added drop-wise within 1 hour. The mixture was stirred at 70° C. for 3 d. The mixture was concentrated to approx. 50 mL and diethylether (70 ml) was added. It was filtered off and washed with diethylether (2×25 ml). The solid was dried under reduced pressure for 4 hours to yield the hydrobromide salt of Ligand 8 (13.9 g, 38.8 mmol, 99%).

The hydrobromide salt of Ligand 8 was neutralized due to poor solubility in toluene and therefore low reactivity in the next step. Neutralization was performed according to the following procedure:

Hydrobromide salt of Ligand 8 (5.00 g, 10.7 mmol) was added to an aqueous solution of sodium hydroxide (4.30 g NaOH in 100 ml H$_2$O). The mixture was stirred for 10 minutes, it was extracted with diethylether (3×50 ml), the combined organic phase was dried over MgSO$_4$, filtered and the solvent removed under reduced pressure to yield the product as a light yellow solid (3.26 g, 8.48 mmol, 79%).

Ligand 8 was characterized by $^1$H NMR (300 MHz) (C$_6$D$_6$) δ (ppm): 0.87 (t, 3H); 1.25 (m, 30H); 1.70 (m, 2H); 3.61 (t, 2H); 4.44 (s, 2H); 7.37-7.50 (m, 3H); 7.83 (d, 1H).

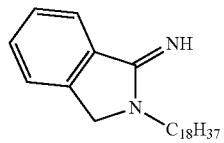

Chemical Formula: C$_{26}$H$_{44}$N$_2$
Molecular Weight: 384.64

Synthesis of Me$_5$CpTiCl$_2$(NC(Ph)(n-C$_{18}$H$_{37}$N) (Compound 8)

To a solution of 2-octadecylisoindolin-1-imine (0.385 g, 1.00 mmol) in toluene (30 ml) was added methyl magnesium bromide solution (1M in Bu$_2$O, 1.00 mL, 1.00 mmol) at 0° C. It was allowed to warm to room temperature and the solution was transferred with a cannula to another flask containing a solution of pentamethylcyclopentadienyl titanium trichloride (0.289 g, 1.00 mmol) in toluene (30 mL). The reaction was heated up to 50° C. and stirred for 72 h. The solution was filtered off, the filtrate was concentrated to approx. 5 mL. The flask was stored at −80° C. After 2 days remaining liquid was removed by decantation and resulting solid was dried under reduced pressure to yield the product as a yellow powder (milligram quantities, <5%).

The powder was characterized by $^1$H NMR (300 MHz) (C$_6$D$_6$) δ (ppm): 0.92 (t, 3H); 1.38 (m, 32H); 2.21 (s, 15H); 3.32 (m, 2H); 3.48 (t, 2H); 6.82 (d, 1H); 7.02 (m, 2H); 7.95 (m, 1H).

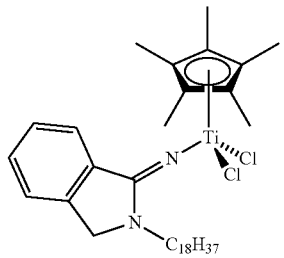

Chemical Formula: C$_{36}$H$_{63}$Cl$_2$N$_2$Ti
Molecular Weight: 642.67

Synthesis of the 2-cyclooctyl-7-fluoroisoindolin-1-imine hydrobromide (Ligand 9)

To a solution of 2-(bromomethyl)-6-fluorobenzonitrile (1.50 g, 7.01 mmol) in toluene (40 ml) a solution of cyclooctylamine (0.892 g, 7.01 mmol) in toluene (20 ml) was added dropwise within 20 min. if was stirred at 50° C. overnight. The solution was concentrated to approx. 10 mL, diethylether (40 ml) was added (40 mL) and filtered off. It was washed with diethylether (3×20 ml), dried under reduced pressure to yield the product as a white solid (0.567 g, 1.88 mmol, 24%).

The powder was characterized by $^1$H NMR (300 MHz) (CDCl$_3$) δ (ppm): 1.55-2.12 (m, 14H); 4.81 (s, 2H); 5.25 (m, 1H); 7.09 (s, 1H); 7.30 (d, 1H); 7.42 (d, 1H); 7.73 (m, 1H); 11.26 (s, 1H).

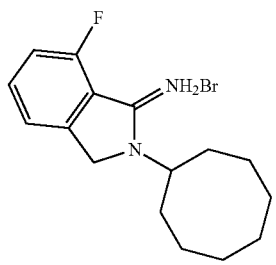

Chemical Formula: C$_{16}$H$_{22}$BrFN$_2$
Molecular Weight: 341.26

Synthesis of Me₅CpTiCl₂(NC(7-fluoro-Ph)(c-C₈H₁₅N) (Compound 9)

To a solution of pentamethylcyclopentadienyl titanium trichloride (0.466 g, 1.61 mmol) and 2-cyclooctyl-7-fluoroisoindolin-1-imine hydrobromide (0.550 g, 1.61 mmol) in toluene (40 ml) was added triethylamine (0.550 mL, 4.00 mmol). The reaction was heated up to 50° C. and stirred for 7 d. The solution was filtered off, the filtrate was concentrated to approx. 5 mL and hexane was added (50 mL). It was filtered off and dried under reduced pressure to yield the product as a yellow powder (508 mg, 0.986 mmol, 61%).

The powder was characterized by ¹H NMR (300 MHz) (C₆D₆) δ (ppm): 1.19-1.69 (m, 14H); 2.23 (s, 15H); 3.48 (s, 2H); 4.48 (m, 1H); 8.50 (d, 1H); 6.64 (m, 1H); 6.83 (m, 1H), ¹⁹F NMR (300 MHz) (C₆D₆) δ (ppm): −113.93 and ¹³C NMR (75 MHz) (C₆D₆) δ (ppm): 140.0; 132.7; 129.1; 127.8; 118.6; 116.0; 53.7; 47.7; 32.4; 27.3; 25.9; 25.2; 13.6.

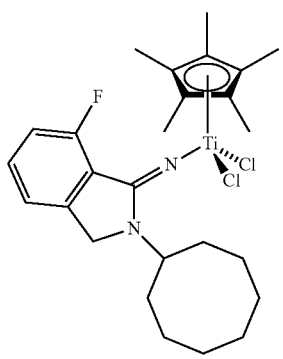

Chemical Formula: C₂₆H₃₅Cl₂FN₂Ti
Molecular Weight: 513.34

Synthesis of Me₅CpTiCl₂(NC(7-fluoro-Ph)(c-C₈H₁₅N) (Compound 9M)

To a solution of Compound 9 (350 mg, 0.682 mmol) in toluene (40 ml) was added methyl magnesium chloride solution (3M in THF, 0.680 ml, 2.04 mmol) dropwise at −80°G. Mixture was allowed to warm to room temperature and stirred overnight. Trimethylsilyl chloride (0.100 ml) was added dropwise and the reaction was stirred for 1 hour. The mixture was concentrated and hexane was added (50 ml). If was filtered off and dried under reduced pressure to yield the product as a yellow powder (84 mg, 0.178 mmol, 27%).

The powder was characterized by ¹H NMR (300 MHz) (C₆D₆) δ (ppm): 0.73 (s, 6H); 1.32-1.65 (m, 14H); 2.12 (s, 15H); 3.71 (s, 2H); 4.58 (m, 1H); 6.60 (d, 1H); 6.68 (d, 1H); 8.88 (m, 1H), 19F NMR (300 MHz) (C₆D₆) δ (ppm): −118.27 and ¹³C NMR (75 MHz) (C₆D₆) δ (ppm): 144.1; 131.8; 120.5; 118.8; 115.8; 115.6; 52.1; 47.5; 47.1; 32.3; 27.4; 26.1; 25.5; 12.6.

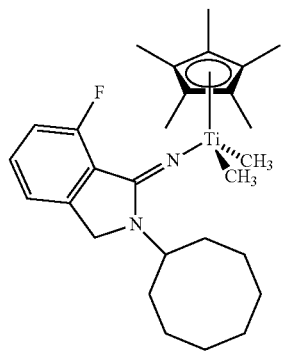

Chemical Formula: C₂₈H₄₁FN₂Ti
Molecular Weight: 472.50

Synthesis of 1-cyclooctylpyrrolidin-2-imine (Ligand 10)

4-Bromobutyronitrile (0.740 g, 5.00 mmol) and cyclooctylamine (0.636 g, 5.00 mmol) were mixed without solvent and heated to 100° C. overnight. The reaction mixture became solid. It was dissolved in dichloromethane (20 ml) and diethylether was added (50 mL). It was filtered off and washed with diethylether (2×25 mL). Again it was dissolved in dichloromethane (40 mL) and dried over MgSO₄. St was filtered off and dried under reduced pressure to yield the hydrobromide salt of the product as a white powder (380 mg, 1.38 mmol, 28%).

The hydrobromide salt of Ligand 10 was neutralized due to poor solubility in toluene and therefore low reactivity in the next step. Neutralization was performed according to the following procedure:

Hydrobromide salt of Ligand 10 (1.300 g, 4.72 mmol) was added to an aqueous solution of sodium hydroxide (4.30 g NaOH in 100 ml H₂O). The mixture was stirred for 10 minutes. It was extracted with diethylether (3×50 mL), the combined organic phase was dried over MgSO₄, filtered and the solvent removed under reduced pressure to yield the product as a light yellow solid (0.69 g, 3.54 mmol, 75%).

The powder was characterized by ¹H NMR (300 MHz) (CDCl₃) δ (ppm): 1.43-1.76 (m, 14H); 2.90 (m, 2H); 2.41 (m, 1H); 2.56 (t, 2H); 3.36 (t, 2H); 4.15 (s, 1H).

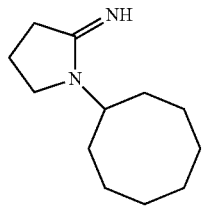

Chemical Formula: C₁₂H₂₂N₂
Molecular Weight: 194.32

Synthesis of (Me₅Cp)(1-cyclooctylpyrrolidine-2-iminato)TiCl₂ (Compound 10)

To a solution of pentamethylcyclopentadienyl titanium trichloride (1.042 g, 3.60 mmol) and Ligand 10 (700 mg, 3.60 mmol) in toluene (30 mL) was added triethylamine (1.25 mL, 9.00 mmol). The reaction was heated up to 50° C. and stirred for 72 h. The solution was filtered off, the filtrate was concentrated to approx. 5 mL and hexane (20 mL) was added. The flask was stored at −80° C. overnight and filtered off. It was recrystallized from toluene/hexanes to yield the product (65 mg, 0.144 mmol, 4% yield).

The powder was characterized by $^1$H NMR (300 MHz) ($C_6D_6$) δ (ppm): 1.08 (m, 2H); 1.20 (m, 2H); 1.35-1.64 (m, 14H); 2.15 (s, 15H); 2.54 (t, 2H); 4.21 (m, 1H),

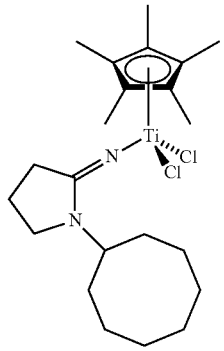

Chemical Formula: $C_{22}H_{41}Cl_2N_2Ti$
Molecular Weight: 452.35

Synthesis of 2-propylisoindolin-1-imine (Ligand 11)

Propylamine (4.11 ml, 50.0 mmol) was added to a solution of 4-Bromomethylbenzonitrile (9.80 g, 50.0 mmol) in toluene (70 ml) and heated to 50° C. overnight. A white solid was filtered off and washed with toluene (40 ml), followed by hexanes (60 ml). It was dried for 12 hours under reduced pressure, yielding the hydrobromide salt of the product as a white powder (10.9 g, 47.7 mmol, 85%).

Due to presence of unreacted propylamine (observable by NMR), a neutralization procedure performed.

2-propylisoindolin-1-imine hydrobromide (12.0 g, 47.0 mmol) of was added to an aqueous solution of sodium hydroxide (9.41 g in 100 ml $H_2O$). The organic phase was removed and further extracted from the aqueous layer using washings of diethylether (4×50 mL). The combined organic phase was then dried over $MgSO_4$, filtered and all volatiles were removed. An oil was formed. Hexanes (10 mL) was added to encourage precipitation but still no solid precipitate formed. Solvent was removed under reduced pressure overnight. The product was dried for another 18 h using molecular sieves. The molecular sieves were decanted off and the solvent evacuated under reduced pressure. Diethylether (15 mL) was added and stirred overnight. Volatiles were removed under reduced pressure and followed by a second washing with diethylether (15 ml) yielding the product as pale pink/purple powder (4.09 g, 23.5 mmol, 50%).

The powder was characterized by $^1$H NMR (300 MHz) ($CDCl_3$) δ (ppm): 7.80 (d, 1H); 7.41-7.30 (m, 3H); 8.20 (s, 1H); 4.35 (s, 2H); 3.45 (t, 2H); 1.71-1.58 (m, 2H); 0.90 (t, 3H),

Chemical Formula: $C_{11}H_{14}N_2$
Molecular Weight: 174.24

Synthesis of $Me_5CpTiCl_2(NC(Ph)(n-C_3H_7N)$ (Compound 11)

Triethylamine (1.93 ml, 13.8 mmol) was added to solution of 2-propylisoindolin-1-imine (0.600 g, 3.45 mmol) and pentamethylcyclopentadienyl titanium trichloride (1.00 g, 3.45 mmol) in toluene (60 ml). It was heated to 80° C. for 72 h. The triethylamine salts were filtered and toluene removed leaving an orange/brown wax-like precipitate. The precipitate was washed with hexanes (80 mL) to aid the removal of excess toluene. All volatiles were then removed under reduced pressure to yield the product as a yellow powder (0.750 g, 1.76 mmol, 51%).

The powder was characterized by $^1$H NMR (300 MHz) ($C_6D_6$) δ (ppm): 7.88-7.85 (m, 1H); 7.09-7.02 (m, 2H); 6.87-6.84 (m, 1H); 3.52 (s, 2H); 3.21 (t, 2H); 2.17 (s, 15H); 1.40-1.28 (m, 2H); 0.80 (t, 3H) and $^{13}$C NMR (75 MHz) ($C_6D_6$) δ (ppm): 160.7; 141.0; 134.7; 131.0; 128.9; 124.6; 122.7; 52.0; 46.4; 22.2; 13.2; 11.5.

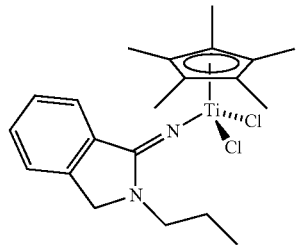

Chemical Formula: $C_{21}H_{28}Cl_2N_2Ti$
Molecular Weight: 427.23

Synthesis of 2-butylisoindolin-1-imine hydrobromide (Ligand 12)

Butylamine (2.47 ml, 25.0 mmol) was added to a solution of 2-Bromomethylbenzonitrile (4.90 g (25.0 mmol) in toluene (70 ml) and heated to 50° C. overnight. The white solid was filtered and washed with toluene (100 ml), followed by hexane (80 ml). It was dried for 12 hours under reduced pressure, yielding the product as a light yellow powder (5.38 g, 20.0 mmol, 80%).

The powder was characterized by $^1$H NMR (300 MHz) ($C_6D_6$) δ (ppm): 10.25 (br s, 1H); 9.78 (br s, 1H); 9.01 (d, 1H); 7.89-7.51 (m, 3H); 4.73 (s, 2H); 4.20 (t, 2H); 1.86-1.78 (m, 2H); 1.61-1.49 (m, 2H); 0.98 (t, 3H).

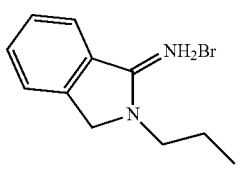

Chemical Formula: C₁₂H₁₇BrN₂
Molecular Weight: 269.18

Synthesis of Me₅CpTiCl₂(NC(Ph)(n-C₃H₇N) (Compound 12)

Triethylamine (1.00 ml, 7.43 mmol) was added to solution of 2-butylisoindolin-1-imine (0.500 g, 1.86 mmol) and pentamethylcyclopentadienyl titanium trichloride (0.54 g, 1.86 mmol) in toluene (35 ml) It was heated to 50° C. overnight. The triethylamine salts were filtered off and all volatiles were then removed under reduced pressure. It was washed with hexanes and dried under reduced pressure to yield the product as a yellow powder (0.64 g, 1.45 mmol, 78%).

The powder was characterized by $^1$H NMR (300 MHz) (C₆D₆) δ (ppm): 7.90-7.87 (m, 1H); 7.08-7.04 (m, 2H); 6.87-6.84 (m, 1H); 3.52 (s, 2H); 3.24 (t, 2H); 2.18 (s, 15H); 1.34-1.18 (m, 4H); 0.89 (t, 3H) and $^{13}$C NMR (75 MHz) (C₆D₆); δ 160.7; 141.0; 134.7; 131.0; 128.3; 126.9; 124.6; 122.8; 52.1; 44.9; 30.9; 20.6; 14.1; 13.3.

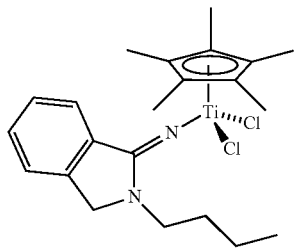

Chemical Formula: C₂₂H₃₀Cl₂N₂Ti
Molecular Weight: 441.26

Synthesis of 2-allylisoindolin-1-imine hydrobromide (Ligand 13)

Allylamine (1.13 ml, 15.0 mmol) was added to a solution of 2-(bromomethyl) benzonitrile (2.94 g, 15.0 mmol) in toluene (20 ml). The solution was heated to 50° C. for 72 hours. The white solid was filtered off, washed with toluene (30 ml), followed by hexanes (30 ml) and dried in vacuo to yield the product as a white powder (3.59 g, 14.2 mmol, 95%).

The powder was characterized by $^1$H NMR (300 MHz) (CDCl₃) δ (ppm); 10.34 (br s, 1H); 9.79 (br s, 1H); 8.99-8.97 (d, 1H); 7.89-7.51 (m, 3H); 6.00-5.93 (ddt, 1H); 5.44-5.38 (dds 1H); 5.39-5.36 (dd, 1H); 4.85-4.83 (d, 2H); 4.74 (s, 2H).

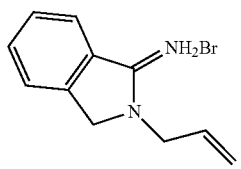

Chemical Formula: C₁₁H₁₃BrN₂
Molecular Weight: 253.14

Synthesis of Me₅CpTiCl₂(NC(Ph)(n-allylamine) (Compound 13)

Triethylamine (2.20 ml, 15.8 mmol) was added to a solution of 2-allylisoindolin-1-imine hydrobromide (1.00 g, 3.95 mmol) and pentamethylcyclopentadienyl titanium trichloride (1.14 g, 3.95 mmol) in toluene (60 ml). The mixture was heated to 50° C. overnight. Whilst maintaining an inert atmosphere, the triethylamine salts (yellow precipitate) were filtered off leaving an orange/red liquid containing the catalyst product. Toluene was removed under reduced pressure to yield the product as a yellow powder (0.540, 1.27 mmol, 32%), The powder was characterized by $^1$H NMR (300 MHz) (C₆D₆) δ (ppm); 7.85-7.82 (dd, 1H); 7.07-7.02 (m, 2H); 6.86-6.83 (d, 1H); 5.57-5.52 (ddt, 1H); 4.96-4.93 (dd, 1H); 4.96-4.90 (dd, 1H); 3.91-3.89 (d, 2H); 3.56 (s, 2H); 2.18 (s, 15H) and $^{13}$C NMR (75 MHz) (C₆D₆) δ (ppm) 170.4; 141.1; 134.4; 133.2; 131.1; 128.3; 127.3; 124.6; 122.8; 117.8; 51.7; 47.1; 13.3.

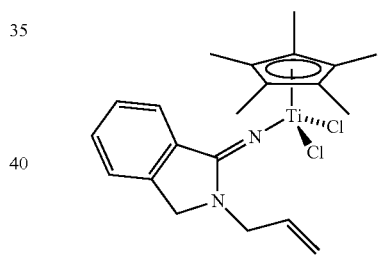

Chemical Formula: C₂₁H₂₆Cl₂N₂Ti
Molecular Weight: 425.22

Synthesis of Me₄PhCpTiCl₂(MC(Ph)(n-allylamine) (Compound 14)

Triethylamine (1.10 ml, 7.90 mmol) was added to a solution of 2-allylisoindolin-1-imine hydrobromide (0.50 g, 1.98 mmol) and tetramethylphenylcyclopentadienyl titanium trichloride (0.69 g, 1.98 mmol) in toluene (40 ml). The mixture was heated to 50° C. overnight. The solution was then filtered to remove triethylamine salts and the toluene was removed under reduced pressure. The product was then re-extracted in hexanes (60 ml) and back filtered, yielding the product as a bright yellow powder (0.480 g, 0.99 mmol, 50%).

The powder was characterized by $^1$H NMR (300 MHz) (C₆D₆) δ (ppm): 7.84-7.80 (m, 1H); 7.73-7.70 (m, 2H); 7.24-6.98 (m, 5H); 6.73-6.70 (m, 1H); 5.42-5.29 (ddt, 1H); 4.88-4.84 (dd, 1H); 4.83-4.76 (dd, 1H); 3.76-3.74 (d, 2H); 3.36 (s, 2H); 2.34 (s, 6H); 2.23 (s, 8H) and $^{13}$C NMR (75 MHz) (C₆D₆) δ (ppm) 160.5; 141.1; 135.6; 134.4; 133.1;

132.1; 131.3; 131.1; 128.3; 128.2; 127.2; 126.6; 125.0; 122.6; 118.0; 51.6; 47.3; 14.5; 13.4.

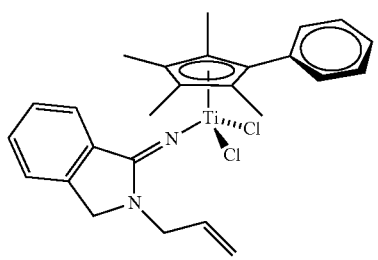

Chemical Formula: C$_{26}$H$_{28}$Cl$_2$N$_2$Ti
Molecular Weight: 487.29

Synthesis of 2-homoallylisoindolin-1-imine hydrobromide (Ligand 15)

But-3-en-1-amine (2.30 ml, 25.0 mmol) was added to a solution of 2-(bromomethyl) benzonitrile (4.90 g, 25.0 mmol) in toluene (70 ml). On addition of the amine, the solution immediately turned from colourless to dark green. The mixture was heated to 50° C. for 72 hours in which a white precipitate (in a pale pink solution) was formed. The precipitate was then filtered and washed with toluene (2×80 ml), followed by hexanes (80 ml). Solvent was removed under reduced pressure to yield the product as a white powder (4.81 g, 18.0 mmol, 72%).

The powder was characterized by $^1$H NMR (300 MHz) (CDCl$_3$) δ (ppm): 10.21 (br s, 1H); 9.77 (br s, 1H); 8.96-8.94 (d, 1H); 7.69-7.50 (m, 3H); 6.08-5.94 (ddt, 1H); 5.18-5.07 (m, 2H); 4.76 (s, 2H); 4.28-4.24 (t, 2H); 2.67-2.60 (q, 1H),

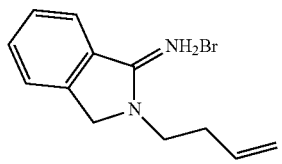

Chemical Formula: C$_{12}$H$_{15}$BrN$_2$
Molecular Weight: 267.16

Synthesis of Me$_5$CpTiCl$_2$(NC(Ph)(n-homoallylamine) (Compound 15)

Triethylamine (1.50 ml, 10.7 mmol) was added to a solution of 2-homoallylisoindolin-1-imine hydrobromide (0.50 g, 2.68 mmol) and pentamethylcyclopentadienyl titanium trichloride (0.78 g, 2.68 mmol) in toluene (40 ml) and heated to 50° C. overnight. Filtration of the triethylamine salts was performed, followed by evaporation of toluene in under reduced pressure.

A purification procedure was then performed by dissolving the product in small amount of toluene (15 ml) and adding around 100 ml of hexanes to other side of double schlenk. Reduced pressure was then applied and the set up was left (without stirring) overnight. Diffusion of around 40 ml of hexanes to the schlenk containing the catalyst product occurred, yielding more yellow precipitate. The precipitate was back filtered and evaporated to dryness yielding the product as a yellow powder (0.360 g, 0.820 mmol, 30%).

The powder was characterized by $^1$H NMR (300 MHz) (C$_6$D$_6$) δ (ppm): 7.88-7.86 (m, 1H); 7.07-7.03 (m, 2H); 6.85-6.83 (m, 1H); 5.79-5.65 (ddt, 1H); 5.10-5.04 (dds 1H); 4.99-4.95 (dd, 1H); 3.53 (s, 2H); 3.35-3.30 (t, 2H); 2.17 (s, 15H) and $^{13}$C NMR (75 MHz) (C$_6$D$_6$) δ (ppm) 160.7; 141.0; 135.3; 134.6; 131.0; 127.1; 124.6; 122.7; 117.4; 52.2; 44.3; 33.2; 13.3.

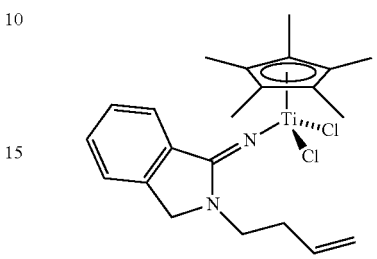

Chemical Formula: C$_{22}$H$_{28}$Cl$_2$N$_2$Ti
Molecular Weight: 439.24

Synthesis of (E)-2-(But-2-en-1yl)isoindolin-1-imine hydrobromide (Ligand 16)

(E) But-2en-1-amine (1.78 g, 25.0 mmol) was added to a solution of 2-(bromomethyl) benzonitrile (4.90 g, 25.0 mmol) in toluene (70 ml). The solution was heated to 50° C. overnight. A white precipitate formed which was filtered (maintaining an inert atmosphere) and washed with hexanes (20 ml) to yield the product as a white powder (5.88 g, 22.0 mmol, 88%).

The powder was characterized by $^1$H NMR (300 MHz) (CDCl$_3$) δ (ppm): 10.20 (br s, 1H); 9.66 (br s, 1H); 8.87-8.85 (d, 1H); 7.67-7.48 (m, 3H); 6.03-5.88 (m, 1H); 5.75-5.59 (m, 1H); 4.70-4.89 (m, 4H); 1.78-1.73 (d, 3H),

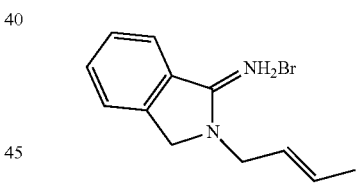

Chemical Formula: C$_{12}$H$_{15}$BrN$_2$
Molecular Weight: 267.16

Synthesis of Me$_5$CpTiCl$_2$(NC(Ph)((E)-2-(but-2en-1-amine)) (Compound 16)

Triethylamine (1.04 ml, 7.49 mmol) was added to a solution of (E)-2-(But-2en-1yl)isoindolin-1-imine hydrobromide (0.500 g, 1.87 mmol) and penta-methylcyclopentadienyl titanium trichloride (0.540 g, 1.87 mmol) in toluene (40 ml) and heated to 50° C. overnight. The triethylamine salts were removed by filtration and the toluene was removed under reduced pressure. The yellow precipitate was then washed with hexanes (30 mi) and dried under reduced pressure to yield the product as a yellow powder (0.220 g, 0.500 mmol, 27%).

The powder was characterized by $^1$H NMR (300 MHz) (C$_6$D$_6$) δ (ppm): 7.88-7.85 (m, 1H); 7.07-7.01 (m, 2H); 6.85-6.82 (m, 1H); 5.46-5.35 (m, 1H); 5.31-5.22 (m, 1H);

3.90-3.88 (d, 2H); 3.56 (s, 2H); 2.17 (s, 15H); 1.50-1.48 (dd, 3H) and 13C NMR (75 MHz) (C$_6$D$_6$) δ (ppm) 160.3; 141.1; 134.8; 131.1; 130.0; 128.3; 127.1; 126.0; 124.6; 122.8; 51.6; 46.6; 17.7; 13.3.

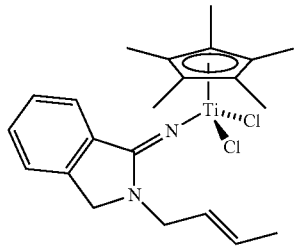

Chemical Formula: C$_{22}$H$_{28}$Cl$_2$N$_2$Ti
Molecular Weight: 439.24

Part II. Batch EP Copolymerisation Examples and Comparative Experiments

The batch co-polymerizations were carried out in a 2-liter batch autoclave equipped with a double intermig and baffles. The reaction temperature was set on 90° C.+/−3° C. (data shown In Table 1 and 2) (120+−3° C. for reactions in Table 3) and controlled by a Lauda Thermostat. The feed streams (solvents and monomers) were purified by contacting with various adsorption media to remove catalyst killing impurities such as water, oxygen and polar compounds as is known to those skilled in the art. During polymerisation the ethylene and propylene monomers were continuously fed to the gas cap of the reactor. The pressure of the reactor was kept constant by a back-pressure valve.

In an inert atmosphere of nitrogen, the reactor was filled with pentamethylheptanes (PMH) (950 ml), MAO (Chemtura, 10 wt. % Al in toluene diluted to 0.10 M), and BHT (Sigma Aldrich 0.2 M in hexanes). The reactor was heated to 90 (data shown in Table 1 and 2) (120° C. for reactions In Table 3), while stirring at 1350 rpm. The reactor was pressurized to 7 bar and conditioned under a determined ratio of ethylene, propylene. After 15 minutes, the catalyst components were added into the reactor and the catalyst vessel was rinsed with PMH (50 mL) subsequently. After 10 minutes of polymerisation, the monomer flow was stopped and the solution was carefully dumped in an Erlenmeyer flask of 2 L, containing a solution of Irganox-1076 in iso-propanol and dried over night at 100° C. under reduced pressure. The polymers were analysed for intrinsic viscosity (IV), for molecular weight distribution (SEC-DV) and composition (FT-IR).

The experimental results are given in Table 1, 2 and 3.

TABLE 1

| Experiment | Metal complex Name | μmol | Cocatalyst BHT μmol/l | Cocatalyst MAO-10T μmol/l | Polymer Analysis C2 wt % | Polymer Analysis C3 wt % | Polymer Analysis IV dl/g |
|---|---|---|---|---|---|---|---|
| Comparative Example 1 | Compound AM | 0.05 | 900 | 450 | 52.6 | 47.4 | 7.5 |
| Comparative Example 2 | Compound B | 0.07 | 900 | 450 | 46.0 | 54.0 | 6.4 |
| Comparative Example 3 | Compound BM | 0.05 | 900 | 450 | — | — | 7.0 |
| Comparative Example 4 | Compound CM | 0.07 | 900 | 450 | 44.2 | 55.8 | 6.8 |
| Inventive Example 1 | Compound 4M | 0.14 | 900 | 450 | 39.7 | 60.3 | 8.5 |
| Inventive Example 2 | Compound 6M | 0.20 | 900 | 450 | 36.7 | 61.3 | 7.8 |
| Inventive Example 3 | Compound 2M | 0.14 | 900 | 450 | 38.4 | 61.6 | 6.2 |
| Inventive Example 4 | Compound 8 | 0.14 | 900 | 450 | 40.7 | 59.3 | 6.7 |
| Inventive Example 5 | Compound 11 | 0.30 | 900 | 450 | 42 | 59 | 9.0 |
| Inventive Example 6 | Compound 12 | 0.30 | 900 | 450 | 42 | 58 | 9.9 |
| Inventive Example 7 | Compound 9M | 0.14 | 900 | 450 | 35.2 | 64.8 | 8.8 |
| Inventive Example 8 | Compound 1M | 0.30 | 900 | 450 | 44.0 | 56.0 | 8.0 |
| Inventive Example 9 | Compound 3M | 0.20 | 900 | 450 | 37.4 | 62.6 | 8.3 |

10 min reaction time, 90° C., 7 barg, propylene 400 NL/h, ethylene 200 NL/h

TABLE 2

| Experiment | Metal complex Name | μmol | Cocatalyst BHT μmol/l | Cocatalyst MAO-10T μmol/l | C2 wt % | C3 wt % | IV dl/g | SEC-DV universal calibration Mn | SEC-DV universal calibration Mw | SEC-DV universal calibration Mz | SEC-DV universal calibration Mw/Mn |
|---|---|---|---|---|---|---|---|---|---|---|---|
| Comparative Example 1 | Compound AM | 0.05 | 900 | 450 | 52.6 | 47.4 | 7.5 | 341 | 680 | 1140 | 2.0 |

TABLE 2-continued

| | | | Cocatalyst | | Polymer Analysis | | | | | | |
|---|---|---|---|---|---|---|---|---|---|---|---|
| | Metal complex | | BHT | MAO-10T | C2 | C3 | IV | SEC-DV universal calibration | | | |
| Experiment | Name | μmol | μmol/l | μmol/l | wt % | wt % | dl/g | Mn | Mw | Mz | Mw/Mn |
| Comparative Example 3 | Compound BM | 0.05 | 900 | 450 | — | — | 7.0 | 304 | 649 | 1037 | 2.1 |
| Comparative Example 4 | Compound CM | 0.07 | 900 | 450 | 44.2 | 55.8 | 6.8 | 290 | 652 | 1129 | 2.2 |
| Inventive Example 1 | Compound 4M | 0.14 | 900 | 450 | 39.7 | 60.3 | 8.5 | 381 | 809 | 1435 | 2.1 |
| Inventive Example 2 | Compound 6M | 0.20 | 900 | 450 | 38.7 | 61.3 | 7.8 | 334 | 705 | 1190 | 2.1 |
| Inventive Example 3 | Compound 2M | 0.14 | 900 | 450 | 38.4 | 61.6 | 8.2 | 387 | 857 | 1636 | 2.2 |

10 min reaction time, 90° C., 7 barg, propylene 400 NL/h, ethylene 200 NL/h

TABLE 3

| | | | Cocatalyst | | Polymer Analysis | | |
|---|---|---|---|---|---|---|---|
| | Metal Complex | | BHT | MAO-10T | C2 | C3 | IV |
| Experiment | Name | μmol | μmol/l | μmol/l | wt % | wt % | dl/g |
| Comparative Example | Compound AM | 0.05 | 900 | 450 | 51.5 | 48.5 | 4.1 |
| Inventive Example 1 | Compound 4M | 0.10 | 900 | 450 | 41.9 | 58.2 | 4.6 |
| Inventive Example 2 | Compound 2M | 0.10 | 900 | 450 | 42.8 | 57.2 | 5.0 |
| Inventive Example 3 | Compound 1M | 0.10 | 900 | 450 | 43.0 | 57.0 | 4.6 |
| Inventive Example 4 | Compound 3M | 0.10 | 900 | 450 | 42 | 58 | 5.1 |

10 min reaction time, 120° C., 7 barg, propylene 400 NL/h, ethylene 140 NL/h

Part III. Batch EPDM Tetropolymerisations (General Procedure)

The batch terpolymerizations were carried out in a 2-liter batch autoclave equipped with a double intermig and baffles. The reaction temperature was set on 90° C. and controlled by a Lauda Thermostat. The feed streams (solvents and monomers) ware purified by contacting with various absorption media to remove catalyst killing impurities such as water, oxygen and polar compounds as is known to those skilled in the art. During polymerisation the ethylene and propylene monomers were continuously fed to the gas cap of the reactor. The pressure of the reactor was kept constant by a back-pressure valve.

In an inert atmosphere of nitrogen, the reactor was filled with pentamethylheptanes PMH (950 mL), MAO-10T (Crompton, 10 wt % in toluene), BHT and 5-ethylidene-2-norbonene (ENB, 2.8 ml). The reactor was heated to 90° C., while stirring at 1350 rpm. The reactor was pressurized and conditioned under a determined ratio of ethylene, propylene and hydrogen (0.35 NL/h). After 15 minutes, the catalyst components were added into the reactor and the catalyst vessel was rinsed with PMH (50 ml) subsequently. After 10 minutes of polymerisation, the monomer flow was stopped and the solution was carefully dumped in an Erlenmeyer flask of 2 L, containing a solution of Irganox-1076 in iso-propanol and dried over night at 100° C. under reduced pressure.

The polymers were analysed for composition (FT-IR).

The experimental results are given in Table 4.

TABLE 4

| | | | Cocatalyst | | Polymer Analysis | | |
|---|---|---|---|---|---|---|---|
| | Metal complex | | BHT | MAO-10T | C2 | C3 | ENB |
| Experiment | Name | μmol | μmol/l | μmol/l | wt % | wt % | wt % |
| Comparative Example 1 | Compound AM | 0.10 | 900 | 450 | 49.1 | 47.2 | 3.73 |
| Comparative Example 2 | Compound CM | 0.07 | 900 | 450 | 44.9 | 51.2 | 4.00 |
| Inventive Example 1 | Compound 2M | 0.14 | 900 | 450 | 40.5 | 54.8 | 4.78 |
| Inventive Example 2 | Compound 8 | 0.14 | 900 | 450 | 35.4 | 59.7 | 4.94 |
| Inventive Example 3 | Compound 11 | 0.30 | 900 | 450 | 37.6 | 57.3 | 5.11 |

TABLE 4-continued

| | | | Cocatalyst | | Polymer Analysis | | |
| | Metal complex | | BHT | MAO-10T | C2 | C3 | ENB |
| Experiment | Name | μmol | μmol/l | μmol/l | wt % | wt % | wt % |
|---|---|---|---|---|---|---|---|
| Inventive Example 4 | Compound 12 | 0.30 | 900 | 450 | 40.8 | 54.0 | 5.17 |
| Inventive Example 5 | Compound 1M | 0.40 | 900 | 450 | 38.7 | 56.0 | 5.22 |
| Inventive Example 6 | Compound 3M | 0.20 | 900 | 450 | 38.5 | 56.5 | 5.01 |
| Inventive Example 7 | Compound 10 | 0.10 | 900 | 450 | 47.9 | 46.0 | 6.16 |

10 min reaction time, 90° C., 7 barg, propylene 400 NL/h, ethylene 200 NL/h, hydrogen 0.35 NL/h Results:

Due to the fact that more catalyst leads to more heat formation the used reactor that was optimized to run at 90° C.+/−3° C. (see tables 1, 2 and 3) and at 120° C.+/−3° C. (see table 4) the amount of catalyst was chosen to give a heat formation in this respective range. Even though the catalyst amount might be different the data can be used to establish certain results.

The parameter to look at are preferably the IV and Mw values as they show what molecular weight magnitudes were achievable. As higher temperatures normally give a lower IV and Mw value the above mentioned lower amount of catalyst in order to limit the temperature to about 90° C. and 120° C. respectively would in ease of the same amount lead to higher temperatures which give lower IV and Mw values which would even amplify this effect rather than to compensate this effect.

The inventive compounds lead to higher IV and Mw values than the comparative examples.

What is claimed is:

1. A metal complex of formula 1

$$CyYML_jX_n \quad \text{(formula 1)}$$

wherein
Cy is a cyclopentadenyl-type ligand;
M is a metal of group 4;
L is a neutral Lewis basic ligand wherein the number of said neutral ligands "j" is 0 to an amount that satisfies the 18-electron rule;
X is an anionic ligand;
n is an integer denoting the number of anionic ligands X and is 1 or 2;
Y is a cyclic amidine-containing ligand moiety represented by formula 2

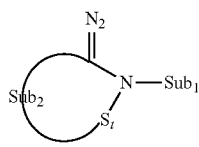

(formula 2)

wherein
the amidine-containing ligand is covalently bonded to the metal M via the imine nitrogen atom $N^2$;

S is a —CH$_2$— unit, and t is the integer number denoting the number of S and is 1-4;
Sub$_1$ is an aliphatic cyclic or linear substituent comprising a group 14 atom through which Sub is bonded to the amine nitrogen atom $N^1$; and
Sub2 is an optionally substituted C2 unit in which the 2 carbon atoms may be sp$^2$ or sp$^3$ hybridized.

2. The metal complex according to claim 1, wherein L is an ether, a thioether, an amine, a tertiary phosphane, an imine, a nitrile, an Isonitrile, a bidentate donor, or an oligodentate donor.

3. The metal complex according to claim 1, wherein j is 0, 1 or 2.

4. The metal complex according to claim 1, wherein M is titanium.

5. The metal complex according to claim 1, wherein X is a halogen atom, a C1-10 alkyl group, a C7-20 aralkyl group, a C6-20 aryl group or a C1-20 hydrocarbon-substituted amino group.

6. The metal complex according to claim 1, wherein Sub1 is an alkyl, alkenyl or alkynyl residue with 1 to 20 carbon atoms, unsubstituted or substituted with halogen, amido, silyl or aryl radicals.

7. The metal complex according to claim 1, wherein Y has the general formula 2a

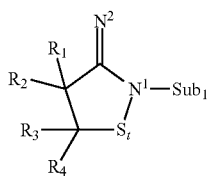

(formula 2a)

wherein $R_1$-$R_4$ are the same or different and each represents a hydrogen atom, a halogen atom, an optionally substituted C1-10 alkyl group, an optionally substituted C1-10 alkoxy group, or the general formula 2b

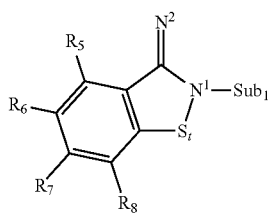

(formula 2b)

wherein $R_5$-$R_6$ are the same or different and each represents a hydrogen atom, a halogen atom, an optionally substituted C1-10 alkyl group, an optionally substituted C1-10 alkoxy group, or the adjacent $R_5$-$R_6$ may be linked to form an aromatic ring optionally substituted.

8. The metal complex of claim 1, wherein Cy is selected from the group consisting of unsubstituted or substituted cyclopentadienyl groups, substituted or unsubstituted indenyl groups, substituted or unsubstituted fluorenyl groups, substituted or unsubstituted tetrahydroindenyl groups, substituted or unsubstituted tetrahydrofluorenyl groups, substituted or unsubstituted octahydrofluorenyl groups, substituted or unsubstituted benzoindenyl groups, substituted or unsubstituted heterocyclopentadienyl groups, substituted or unsubstituted heteroindenyl groups, substituted or unsubstituted heterofluorenyl groups, or their isomers.

9. The metal complex of claim 1, wherein:
Cy is 1,2,3,4,5-pentamethyl-cyclopentadienyl;
M is titanium;
L is an ether, a thioether, an amine, a tertiary phosphane, an imine, a nitrile, an isonitrile, a bidentate donor, or an oligodentate donor;
j is 0, 1 or 2;
X is a halogen atom, a C1-10 alkyl group, a C7-20 aralkyl group, a C6-20 aryl group or a C1-20 hydrocarbon-substituted amino group;
n is 2; and
Y is
a ligand moiety of the general formula 2a

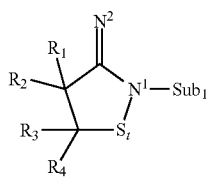

(formula 2a)

wherein $R_1$-$R_4$ are the same or different and each represents a hydrogen atom, a halogen atom, an optionally substituted C1-10 alkyl group, an optionally substituted C1-10 alkoxy group, or a ligand moiety of the general formula 2b

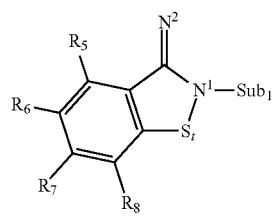

(formula 2b)

wherein $R_5$-$R_6$ are the same or different and each represents a hydrogen atom, a halogen atom, an optionally substituted C1-10 alkyl group, an optionally substituted C1-10 alkoxy group, or the adjacent $R_5$-$R_8$ may be linked to form an aromatic ring optionally substituted,
wherein:
Sub1 is an alkyl, alkenyl or alkynyl residue with 1 to 20 carbon atoms, unsubstituted or substituted with halogen, amido, silyl or aryl radicals,
S is a —$CH_2$— unit, and
t is 1.

10. A process for manufacturing the metal complex according to claim 1, wherein a metal complex of the formula 3

$$CyML_jX_n \qquad \text{(formula 3)}$$

is reacted with YH or YH.HHal, the hydrohalogen acid salt of YH wherein Hal is halogen.

11. A catalyst system comprising
a) a metal complex of the formula 1 according to claim 1, and
b) a scavenger.

12. The catalyst system according to claim 11, wherein the scavenger b) is a hydrocarbyl of a metal or metalloid of group 1-13 or its reaction products with at least one sterically hindered compound containing a group 15 or 16 atom.

13. A process for the preparation of a polymer by polymerizing at least one olefinic monomer, the process comprising contacting at least one olefinic monomer with the metal complex according to claim 1.

14. The process according to claim 13, wherein:
the metal complex is in the form of a catalyst system comprising the metal complex and a scavenger; and
the at least one olefinic monomer comprises ethylene and at least one $C_3$-$C_{12}$-α-olefin.

15. The process according to claim 14, wherein the at least one olefinic monomer comprises ethylene, at least one $C_{3-12}$ alpha olefin and at least one non-conjugated diene.

16. The process according to claim 15, wherein the at least one non-conjugated diene is selected from the group consisting of 5-methylene-2-norbornene, 5-ethylidene-2-norbornene, 5-vinylnorbornene, 2,5-norbornadiene, dicyctopentadiene and vinylcyclohexene.

* * * * *